US010682498B2

(12) United States Patent
Doering et al.

(10) Patent No.: US 10,682,498 B2
(45) Date of Patent: Jun. 16, 2020

(54) LIGHT SHIELDS FOR CATHETER SENSORS

(71) Applicant: Silicon Microstructures, Inc., Milpitas, CA (US)

(72) Inventors: Holger Doering, Sunnyvale, CA (US); Stephen C. Terry, Palo Alto, CA (US); Justin Gaynor, Mountain View, CA (US); Omar Abed, San Jose, CA (US); Fernando Alfaro, Redwood City, CA (US)

(73) Assignee: SILICON MICROSTRUCTURES, INC., Milpitas, CA (US)

( * ) Notice: Subject to any disclaimer, the term of this patent is extended or adjusted under 35 U.S.C. 154(b) by 228 days.

(21) Appl. No.: 15/785,024

(22) Filed: Oct. 16, 2017

(65) Prior Publication Data

US 2018/0099120 A1  Apr. 12, 2018

Related U.S. Application Data

(63) Continuation-in-part of application No. 15/295,051, filed on Oct. 17, 2016, which is a continuation of application No. 15/227,370, filed on Aug. 3, 2016, now Pat. No. 10,041,851.

(60) Provisional application No. 62/232,394, filed on Sep. 24, 2015.

(51) Int. Cl.
*A61M 25/01* (2006.01)
*A61M 25/00* (2006.01)
*G01L 27/00* (2006.01)
*G01L 19/00* (2006.01)
*A61B 90/00* (2016.01)
(Continued)

(52) U.S. Cl.
CPC ......... *A61M 25/0147* (2013.01); *A61B 90/06* (2016.02); *A61M 25/0009* (2013.01); *G01L 9/0042* (2013.01); *G01L 9/0052* (2013.01); *G01L 19/0069* (2013.01); *G01L 27/005* (2013.01); *A61B 2017/00323* (2013.01); *A61B 2090/064* (2016.02); *A61B 2562/18* (2013.01); *A61B 2562/185* (2013.01); *A61M 2025/0002* (2013.01); *A61M 2025/0166* (2013.01)

(58) Field of Classification Search
None
See application file for complete search history.

(56) References Cited

U.S. PATENT DOCUMENTS 4,274,423 A  6/1981 Mizuno et al.
4,343,197 A  8/1982 Suzuki et al.
4,372,041 A  2/1983 Winkelman
(Continued)

FOREIGN PATENT DOCUMENTS

DE  112013001218  1/2015
JP  H07225240 A  8/1995
(Continued)

OTHER PUBLICATIONS

U.S. Appl. No. 15/227,370 , "Notice of Allowance", dated Mar. 26, 2018, 8 pages.
(Continued)

*Primary Examiner* — Natalie Huls
*Assistant Examiner* — Jermaine L Jenkins

(57) ABSTRACT

Pressure sensors and associated structures that may have reduced light sensitivity. An example may provide structures reducing light at a component on a membrane of a pressure sensor.

22 Claims, 13 Drawing Sheets

(51) Int. Cl.
*G01L 9/00* (2006.01)
*A61B 17/00* (2006.01)

(56) References Cited

U.S. PATENT DOCUMENTS

| | | | |
|---|---|---|---|
| 4,576,181 A | 3/1986 | Wallace et al. | |
| 4,809,704 A | 3/1989 | Sogawa et al. | |
| 5,551,301 A | 9/1996 | Cowan | |
| 5,551,501 A | 9/1996 | Davis et al. | |
| 5,902,933 A | 5/1999 | Bingo et al. | |
| 6,030,709 A | 2/2000 | Jensen et al. | |
| 6,247,369 B1 | 6/2001 | Chapman et al. | |
| 6,255,728 B1 | 7/2001 | Nasiri et al. | |
| 6,644,125 B1 | 11/2003 | Siess et al. | |
| 7,127,278 B2* | 10/2006 | Melker | A61B 5/0873 600/340 |
| 8,439,890 B2* | 5/2013 | Beyar | A61F 2/958 604/507 |
| 8,714,021 B2 | 5/2014 | Gamage | |
| 8,801,461 B2 | 8/2014 | Kim et al. | |
| 9,176,018 B2 | 11/2015 | Qi | |
| 9,289,137 B2 | 3/2016 | Corl | |
| 9,314,584 B1* | 4/2016 | Riley | A61M 25/00 |
| 9,385,478 B2 | 7/2016 | Kim et al. | |
| 9,391,002 B2 | 7/2016 | Belov | |
| 9,557,237 B2 | 1/2017 | McNeal et al. | |
| 9,928,762 B2* | 3/2018 | Franklin | G09F 13/0413 |
| 10,041,851 B2 | 8/2018 | Doering et al. | |
| 2003/0007890 A1* | 1/2003 | Mitani | G01L 9/0042 422/400 |
| 2003/0052702 A1 | 3/2003 | Auburger et al. | |
| 2004/0118214 A1 | 6/2004 | McDonald et al. | |
| 2008/0114254 A1* | 5/2008 | Matcovitch | A61B 5/0097 600/463 |
| 2008/0194933 A1* | 8/2008 | Kunze | A61B 5/1459 600/339 |
| 2010/0308791 A1 | 12/2010 | Gowrishetty et al. | |
| 2012/0147384 A1 | 6/2012 | Swiergiel et al. | |
| 2013/0041227 A1* | 2/2013 | Chan | A61M 16/0488 600/199 |
| 2014/0238142 A1 | 8/2014 | Gamage et al. | |
| 2014/0242740 A1 | 8/2014 | Qi | |
| 2014/0331777 A1* | 11/2014 | Tomita | G01L 9/06 73/754 |
| 2015/0001733 A1 | 1/2015 | Karhade et al. | |
| 2017/0089788 A1 | 3/2017 | Doering et al. | |
| 2017/0131167 A1 | 5/2017 | Doering et al. | |
| 2018/0099120 A1 | 4/2018 | Doering et al. | |

FOREIGN PATENT DOCUMENTS

| | | |
|---|---|---|
| JP | H08111260 A | 4/1996 |
| JP | H10103911 | 4/1998 |
| JP | 5168184 B2 | 2/2009 |
| JP | 5318737 B2 | 7/2013 |
| WO | WO 2017/053943 A1 | 3/2017 |
| WO | WO 2017/053943 A8 | 5/2017 |
| WO | 2018075410 | 4/2018 |

OTHER PUBLICATIONS

U.S. Appl. No. 15/295,051, "Non-Final Office Action", dated Aug. 8, 2018, 13 pages.
PCT/US2016/053713, "International Preliminary Report on Patentability", dated Apr. 5, 2018, 8 pages.
PCT/US2017/056813, "International Search Report and Written Opinion", dated Mar. 19, 2018, 15 pages.
PCT/US2017/056813, "International Search Report and Written Opinion", dated Jul. 2, 2018, 16 pages.
PCT/US2017/056813, "Invitation to Pay Add'l Fees and Partial Search Report", dated Jan. 24, 2018, 11 pages.
Notification of Transmittal of the International Search Report and the Written Opinion of the International Searching Authority, or Declaration for International Patent Application No. PCT/US2016/053713 dated Jan. 5, 2017, 12 pages.
Office Action (English translation) dated Jan. 30, 2019 in Chinese Patent Application No. 201680055360.9, 7 pages.
Office Action dated Aug. 26, 2019 in U.S. Appl. No. 15/295,051, 12 pages.
Office Action (English translation) dated Sep. 27, 2019 in Chinese Patent Application No. 201680055360.9, 6 pages.

* cited by examiner

LIGHT SHIELDS FOR CATHETER SENSORS

CROSS-REFERENCE TO RELATED APPLICATIONS

This application is a continuation-in-part of U.S. application Ser. No. 15/295,051, filed Oct. 17, 2016, which is a continuation-in-part of U.S. application Ser. No. 15/227,370, filed Aug. 3, 2016, which is a nonprovisional of U.S. provisional application No. 62/232,394, filed Sep. 24, 2015, which are incorporated by reference.

BACKGROUND

Pressure sensors have become ubiquitous the past few years as they have found their way into many types of products. Utilized in automotive, industrial, consumer, and medical products, the demand for pressure sensors has skyrocketed and shows no signs of abating.

Pressure sensor systems may include pressure sensors as well as other components. Pressure sensors may typically include a diaphragm or membrane. This membrane may be formed by creating the Wheatstone bridge in a silicon wafer, then etching away the silicon from the opposite surface until a thin layer of silicon is formed beneath the Wheatstone bridge. The resulting membrane may be surrounded by a thicker, non-etched silicon wafer portion or frame. When a pressure sensor in a pressure sensor system experiences a pressure, the membrane may respond by changing shape. This change in shape may cause one or more characteristics of electronic components on the membrane to change. These changing characteristics may be measured, and from these measurements, the pressure may be determined.

In some applications, it may be desirable that a pressure sensor have a specific form factor. For example, in many applications, it may be important that the pressure sensor be small, or have a thin form factor, or both.

But pressure sensors having these small form-factors may be difficult to assemble into larger components. For example, these pressure sensors may be too small to use with traditional semiconductor assembly tools for wire bonding or flip-chip assembly. Absent these well-established techniques for electrically connecting pressure sensors to their surroundings, device manufacturers have turned to expensive and laborious manual assembly techniques, with their drawbacks in cost, quality and yield.

Thus, what are needed are pressure sensors and associated structures that may facilitate the use of automated assembly processes and tools.

SUMMARY

Accordingly, embodiments of the present invention may provide pressure sensors and associated structures that may facilitate the use of automated assembly processes and tools. An illustrative embodiment of the present invention may provide pressure sensor systems including pressure sensors and structures for aligning interconnect wires, such as bond wires or other wires, to pressure sensor bondpads in order to facilitate the use of these automated assembly processes and tools.

In these and other illustrative embodiments of the present invention, multiple wires may be joined together in a coplanar arrangement, where the spacings of the wires may match a spacing of bondpads on a pressure sensor. This may be achieved using various alignment structures in these and other embodiments of the present invention. These alignment structures may include wire combs, spacers, insulation layers around individual wires or group of wires, and other structures.

These and other illustrative embodiments of the present invention may provide a pressure sensor system including a pressure sensor, wires, and a wire comb for aligning the wires to bondpads of the pressure sensor. The wires may be bare wires or they may be insulated along a portion of their length. The wires may be inserted into slots along a top, bottom, or sides (or combination thereof) of the wire comb. In these and other embodiments of the present invention, the wires may be inserted through passages in the wire comb. The slots or passages may be spaced to match a spacing of the bondpads of the pressure sensor. The slots or passages may further match a topology of a surface of the pressure sensor where the bondpads are located. Typically this topology may be planar, but other topologies are possible. The wire comb may hold the wires in place to facilitate the use of automated processes and tools in attaching the wires to the bondpads. Due to size constraints, the wire comb may be separate from and not attached directly to the pressure sensor, though the wire comb may be attached indirectly through the wires to the pressure sensor. In these and other embodiments of the present invention, the wire comb may be attached directly to the pressure sensor, for example by epoxy or other potting material placed over the bondpads. The wire comb may be formed of plastic, metal, or other nonconductive or conductive material.

These and other illustrative embodiments of the present invention may provide a pressure sensor system including a pressure sensor, wires, and spacers for aligning the wires to bondpads of the pressure sensor. The wires may be bare wires or they may be insulated along a portion of their length. The spacers may be between the wires or between and fully or partially around the wires. The spacers may hold the wires in a configuration to match a spacing of the bondpads of the pressure sensor. The spacers may hold the wires in a configuration to match a topology of a surface of the pressure sensor where the bondpads are located. Typically this topology may be planar, but other topologies are possible. The spacers may hold the wires in place to facilitate the use of automated processes and tools in attaching the wires to the bondpads. Due to size constraints, the spacers may be separate from and not attached directly to the pressure sensor, though the spacers may be attached indirectly through the wires to the pressure sensor. In these and other embodiments of the present invention, the spacers may be attached directly to the pressure sensor, for example by epoxy or other potting material placed over the bondpads. The spacers may be formed of plastic, metal, or other nonconductive or conductive material.

These and other illustrative embodiments of the present invention may provide a pressure sensor system including a pressure sensor, wires, and an insulation layer around each of the wires. One or more of the wires may have a modified insulation layer. The insulation layer may be modified such that the wires are aligned to bondpads of the pressure sensor. The wires may be insulated along a portion of their length. The existing insulation layer may be modified such that wires may be placed adjacent to each other and have a resulting spacing that matches a spacing of the bondpads of the pressure sensor. That is, the insulation layer around the wires may be thickened, thinned, flattened, or they may be modified in other ways. The wires may be fixed to each other to facilitate the use of automated processes and tools in attaching the wires to the bondpads. The wires may be fixed to each other either by gluing or melting together the insulation layer surrounding each wire. For example, the wires may be heated and rolled such that the insulation layer of the wires bond to the insulation layer of adjacent wires. The wires may also be arranged to match a topology of a surface of the pressure sensor where the bondpads are located. Typically this topology may be planar and the wires may be in a coplanar arrangement, but other topologies are possible. Due to size constraints, the insulation layer around the wires may be separate from and may not typically be attached directly to the pressure sensor. In these and other embodiments of the present invention, the insulation layers may be attached directly to the pressure sensor, for example by epoxy or other potting material placed over the bondpads. In these and other embodiments of the present invention, the insulation layer or layers may be formed of plastic, polymers, or other material, and may be formed by extrusion or other process.

These and other illustrative embodiments of the present invention may provide a pressure sensor system including a pressure sensor, wires, and an insulation layer around each of the wires. The wires may have an insulation layer that is formed such that adjacent wires are aligned with bondpads of the pressure sensor. The wires may be insulated along a portion of their length. The insulation layer may be formed around each wire such that the wires may be placed adjacent to each other and have a resulting spacing that matches a spacing of the bondpads of the pressure sensor. That is, the insulation layer around the wires may be the thickness that is needed to provide a spacing between the wires that matches a spacing of the bondpads. The wires may be fixed to each other to facilitate the use of automated processes and tools in attaching the wires to the bondpads. For example, the wires may be heated and rolled such that the insulation layer of the wires bond to the insulation layer of adjacent wires. The wires may also be arranged to match a topology of a surface of the pressure sensor where the bondpads are located. Typically this topology may be planar, but other topologies are possible. Due to size constraints, the insulation layer around the wires may be separate from and may not typically be attached directly to the pressure sensor. In these and other embodiments of the present invention, the insulation layers may be attached directly to the pressure sensor, for example by epoxy or other potting material placed over the bondpads. In these and other embodiments of the present invention, the insulation layer or layers may be formed of plastic, polymers, or other material, and may be formed by extrusion or other process.

These and other illustrative embodiments of the present invention may provide a pressure sensor system including a pressure sensor, wires, and a common insulation layer that may be formed around the wires. The common insulation layer may be formed such that the wires are aligned to bondpads of the pressure sensor. The wires may be insulated along a portion of their length by a common insulation layer. For example, the wires may be placed in an arrangement having a spacing that matches a spacing of the bondpads. A common insulation layer may then be formed around the wires. The common insulation layer may fix the wires to each other to further facilitate the use of automated equipment. The wires may also be arranged to match a topology of a surface of the pressure sensor where the bondpads are located. Typically this topology may be planar, but other topologies are possible. Due to size constraints, the insulation layer around the wires may be separate from and may not typically be attached directly to the pressure sensor. In these and other embodiments of the present invention, the insulation layer or layers may be attached directly to the pressure sensor, for example by epoxy or other potting material placed over the bondpads. In these and other embodiments of the present invention, the insulation layer or layers may be formed of plastic, polymers, or other material, and may be formed by extrusion or other process.

Automated processes and tools may be employed to electrically and physically join the wires to the pressure sensor bondpads. Initially, an insulation layer may be stripped from the wires. This may be done with a laser or lasers, but may also be accomplished with heat, chemical, or mechanical means, for example by chemical etching. The exposed conductors of the wires may then be cut, preferably without damaging or bending the wires, or otherwise destroying the spacing required for automated assembly. Laser cutting may be used for this purpose.

The now-isolated wire tips may then be aligned with the bondpads of the sensor. Various methods may be employed to electrically and physically join the wires to the bondpads. First, the bondpads may be coated with a solder during wafer manufacture. The die may then be heated to melt the solder, and then the wires may be brought into contact with the molten solder. Once this has been achieved, the heat source may be removed, allowing the solder to cool and harden onto the wire. The wires may be attached one at a time, two or more at a time, or all wires may be attached in a single operation.

These and other embodiments of the present invention may use compression bonding to attach the wires to the bondpads. In these and other embodiments of the present invention, two closely-spaced electrodes may be brought into contact with the wire. A current may be passed from one electrode through the wire and to the second electrode. The electrodes may pressed down on the wire, and the combination of heat and pressure may weld the wires to the bondpads. The wires may be attached one at a time, two or more at a time, or all wires may be attached in a single operation.

In these and other embodiments of the present invention, during compression bonding, no current is passed through the wire. Instead, current may be passed through a highly-resistive region between the two electrodes, resulting in heat generation. The electrodes may be pressed down on the wire, and the combination of heat and pressure may weld the wires to the bondpads. The wires may be attached one at a time, two or more at a time, or all wires may be attached in a single operation.

These and other embodiments of the present invention may instead rely on heat and pressure applied to the wires. The sensors may be placed on a hotplate or other heat source, or the heat may be applied from above the wires as the wires are pressed onto the bondpads. The wires may be attached one at a time, two or more at a time, or all wires may be attached in a single operation.

The wires and bondpads in these pressure sensor systems may be arranged symmetrically in a lateral direction. This may result in the wires being attached to the bondpads in a reversed or mirrored configuration during assembly. This error in attachment may necessitate reworking of the pressure sensor system and may even result in yield loss. Accordingly, embodiments of the present invention may provide alignment structures that are asymmetrical. For example, where wires are held in a wire comb, the slots or openings in the wire comb may be unevenly spaced in a lateral direction. The bondpads on the pressure sensor may also be unevenly spaced in the lateral direction. In other embodiments of the present invention, spacers may provide different spacings between the wires. In still other embodiments of the present invention, wires may have mismatched widths for their insulation layers.

To electrically isolate the bondpads from one another, these and other embodiments of the present invention may cover the bondpads of a pressure sensor, along with the wires soldered or otherwise attached to them, with an insulating material such as epoxy, adhesive, sealant, or other potting material or substance or the like. In addition to providing an electrical insulation layer, this may provide mechanical protection of the delicate solder bonds during assembly, shipping and operation. This material may be dispensed in liquid form and then cured by heat, exposure to humidity, UV irradiation or similar techniques. Unfortunately, the flow of the epoxy or other potting material or sealant may be difficult to control.

Accordingly, these and other illustrative embodiments of the present invention may provide a pressure sensor having a blocking structure for blocking or limiting a flow of epoxy or other adhesive or other potting material when the epoxy or other potting material is placed over one or more bondpads on a surface of the pressure sensor. The blocking structure may be between a number of bondpads and a device identifier or the pressure sensor membrane (or both). The bondpads may be wire bonded, soldered, welded, or attached using other technique and covered with epoxy or other potting material. The blocking structure may protect the device identifier or pressure sensor membrane (or both) from being covered by the epoxy or other potting material. The device identifier may include date information, manufacturer identification information, manufacturing site identification information, mask layer revision information, and other types of information.

The blocking structure may be a trench that is formed by etching along with a device identifier. The trench and device identifier may be etched using a KOH etch, laser etch, a deep-reactive ion etch (DRIE), or other type of etch. The trench may be located between the device identifier and a number of bondpads. After wires have been connected to the bondpads, an epoxy or other potting material may be placed over the bondpads. The trench may halt, block, or otherwise stop the flow of epoxy or other potting material from reaching the device identifier or the pressure sensor membrane (or both). This may increase yield by preventing losses that otherwise may result when the epoxy or other potting material flows enough to cover the device identifier or the pressure sensor membrane (or both). This trench may also lead to more consistent placement of the epoxy or other potting material and a more consistent covering of the bondpads by the epoxy or other potting material.

In these and other embodiments of the present invention, the blocking structure may be a bar that is formed by deposition, plating, by forming solder bumps or other techniques along with the bondpads. The bar may be located between the device identifier or the pressure sensor membrane (or both) and a number of bondpads. After wires have been connected to the bondpads, an epoxy or other potting material may be placed over the bondpads. As with the trench, the bar may halt, block, or otherwise stop the flow of epoxy or other potting material from reaching the device identifier or the pressure sensor membrane (or both). As before, this may increase yield and lead to more consistent placement of the epoxy or other potting material and a more consistent covering of the bondpads by the epoxy or other potting material.

In these and other embodiments of the present invention, the blocking structure may include both a bar and a trench, two or more bars, two or more trenches, or combination thereof. In these embodiments of the present invention, a bar may be between a trench and the device identifier, a trench may be between a bar and the device identifier, two bars may be between one or more bondpads and the device identifier or the pressure sensor membrane (or both), or two trenches may be between one or more bondpads and the device identifier or the pressure sensor membrane (or both). Also, in other embodiments of the present invention, the blocking structure may be used to protect other features on the pressure sensor, such as other bondpads, the sensor membrane, other electrical components formed in or placed on the pressure sensor, or other structure.

These and other embodiments of the present invention may provide a pressure sensor having side tabs that may be used when the pressure sensor is held in a fixture. The side tabs may then be separated or otherwise removed before use.

These tabs may be formed with the pressure sensor as extensions on each side of the pressure sensor near the bondpads. In other embodiments of the present invention, they may be attached to another portion of a pressure sensor. The tabs may be placed in a fixture to hold the pressure sensor in place during further manufacturing, for example during the attachment of wires to the bondpads and the application of an epoxy or other adhesive or potting material or substance over the bondpads. Holes may be drilled or etched in the tabs near the body of the pressure sensor. The holes may be etched using a KOH etch, a DRIE, laser, or other etching technique. These holes may facilitate the removal of the tabs. For example, in one embodiment of the present invention, the holes may act as perforations that enable the side tabs to be snapped off the pressure sensor. In other embodiments of the present invention, the tabs may be removed by sawing, cutting, laser etching, or other technique, either with or without the presence of the holes. These tabs may improve and simplify the process of attaching wires to the pressure sensor, the application of an adhesive or potting material or substance over the wires, or other manufacturing steps. This improvement and simplification may reduce yield losses and reduce overall manufacturing costs.

These and other embodiments of the present invention may provide pressure sensors having a handle portion where the handle area may be less likely to contact a housing for a pressure sensor during use. Specifically, the handle may be thinned to avoid contacting a housing while in use. The thicker base portion may be epoxied or otherwise fixed with an adhesive to a bottom of the housing. The thinner handle may also prevent the migration of the epoxy or potting material under the handle, which could otherwise stiffen and reduce a sensitivity of the pressure sensor. A membrane may be formed in the thinner handle portion of the pressure sensor. A number of bondpads may be formed in the thicker base portion of the pressure sensor. This may reduce the number of pressure sensors that are in contact with a housing after manufacturing, thereby increasing yield and reducing manufacturing costs.

These and other embodiments of the present invention may provide a pressure sensor having a number of bondpads in a thicker base portion. The bondpads may be staggered such that they have a different height relative to a bottom edge of the pressure sensor. These differing heights may facilitate the attachment of wires to the bondpads during the assembly of systems that include these pressure sensors. This may improve yield and reduce manufacturing costs.

These and other embodiments of the present invention may provide pressure sensors that may be used in various applications. For example, they may be used in catheters, biopsy equipment, or other medical applications, and in other types of applications. In some of these applications, a pressure sensor may be exposed to light, such as from an endoscope. In some embodiments of the present invention, this may be desirable and it may not be necessary to take preventive measures. In other embodiments of the present invention, the presence of light may shift or alter pressure sensor readings in an undesirable manner. For example, light may change characteristics of p-n junctions of resistors, transistors, or other components on or near the pressure sensor membrane. This may alter measurements of resistance values or other parameters of the components, thereby skewing the resulting pressure readings in an undesirable manner.

Accordingly, embodiments of the present invention may provide structures for blocking light for all or some of the components on a pressure sensor. For example, a pressure sensor may be placed in an opaque package or housing. In these and other embodiments of the present invention, a layer of metal or other material may be formed over some or all of a number of components on or near a membrane of the pressure sensor. This layer may be gold, copper, aluminum or other material. This layer may be attached to the pressure sensor using a material with an adhesive quality, such as tantalum, titanium-tungsten, titanium, chromium, or other metal or other material. That is, this layer may be over an adhesion layer of tantalum, titanium-tungsten, titanium, chromium, or other metal or other material. The material for the layer, as well as the adhesion layer, may be chosen for its softness or other property such that its presence has a minimized effect on characteristics of components on the pressure sensor. These layers may be formed by physical vapor deposition (PVD), plating, sputtering, or other process. These layers may be formed while the pressure sensors are attached as a wafer before singulation. These layers may be omitted from the bondpads and other portions of the pressure sensor. In these and other embodiments of the present invention, one or more layers of a pressure sensor may be altered or modified, or additional layers may be added, to reduce or block light. For example, antireflective coatings, such as buried antireflective coatings, may be used to block light from reaching the p-n junctions of the pressure sensor components.

In these and other embodiments of the present invention, the layer of metal over the membrane may form a light shield to block light from reaching components on the membrane. This light shield may be protected by encapsulation with epoxy or other material. But since the pressure sensor may be inserted in a human body, it may be desirable to reduce its size. Accordingly, embodiments of the present invention may leave the light shield exposed and not encapsulated with epoxy or other substances. In these and other embodiments of the present invention, a thin protective layer, as opposed to a full encapsulation, may be applied over the light shield.

Since the light shield may be exposed and not encapsulated, it may come into direct contact with human body tissue during its use. Accordingly, the light shield may be left electrically floating and not connected to ground or other voltage potential. This may help to prevent the formation of electrical pathways through the human body and pressure sensor. It may also prevent reduced battery life from electrical leakage pathways in battery-powered devices.

It may also be desirable to be able to track a temperature of the pressure sensor's environment. Unfortunately, there may not be sufficient area to place temperature sensing circuitry on the pressure sensor. Instead, measurements of resistors on the membrane may be made. Temperature changes may cause each resistor on the membrane to change in the same way. This is in contrast to changes in pressure, which may cause each resistor to change differently. Accordingly, these two effects may be separated to track temperature and pressure independently. Calibration and testing routines may be done during or after manufacturing to generate data tables and formulae that may be used to translate resistance changes to pressure and temperature variations.

Various embodiments of the present invention may incorporate one or more of these and the other features described herein. A better understanding of the nature and advantages of the present invention may be gained by reference to the following detailed description and the accompanying drawings.

DESCRIPTION OF ILLUSTRATIVE EMBODIMENTS

Figure 1:
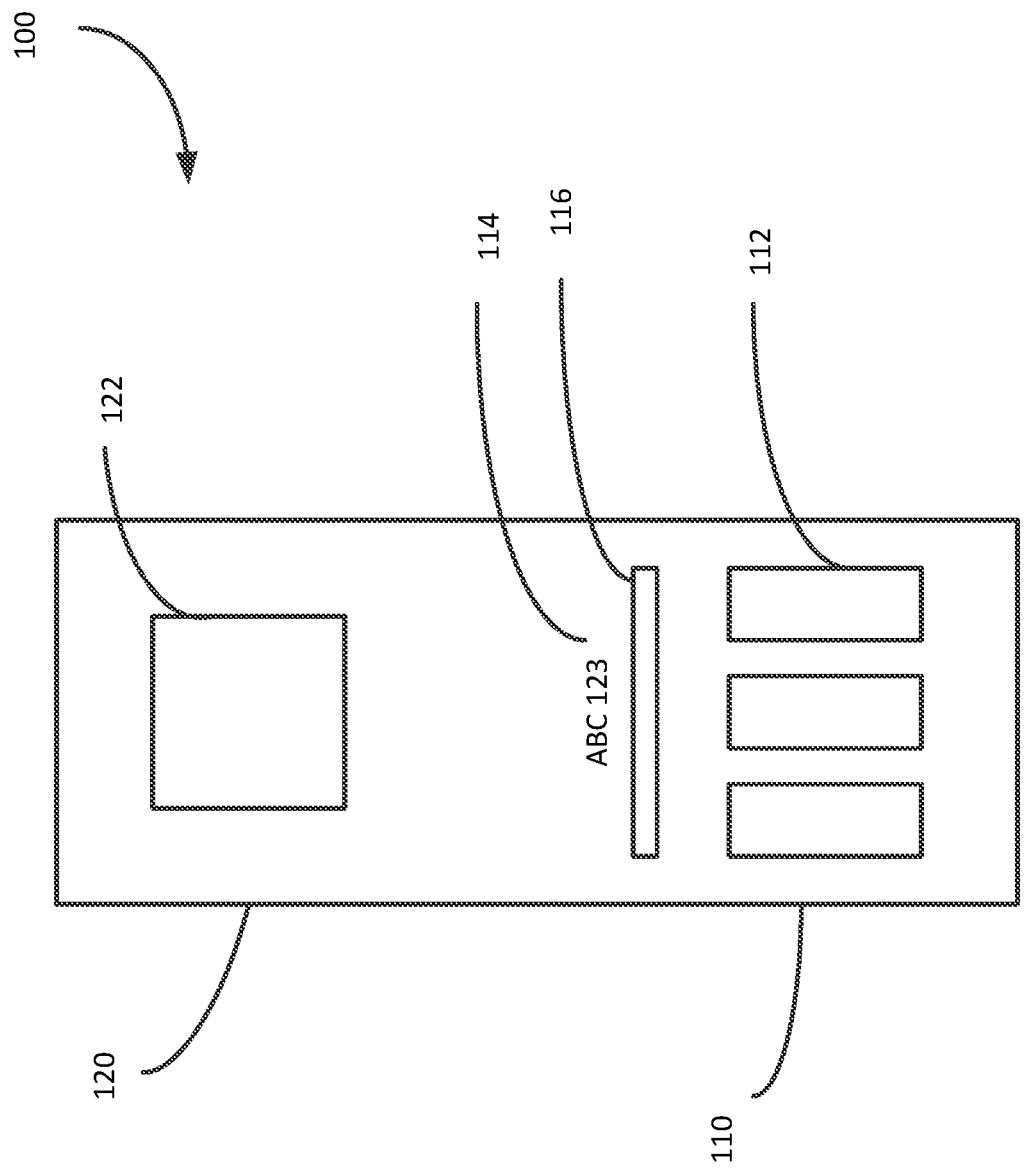
FIG. 1 is a top view of a pressure sensor having a blocking structure according to an embodiment of the present invention.

FIG. 1 is a top view of a pressure sensor according to an embodiment of the present invention. This figure, as with the other included figures, is shown for illustrative purposes and does not limit either the possible embodiments of the present invention or the claims.

Pressure sensor 100 may include a base portion 110 and handle portion 120. Base portion 110 may include a number of bondpads 112 and a device identifier 114. Handle portion 120 may include membrane 122. A number of resistors or other components (not shown) may be formed on or near membrane 122. These components may be used to form a Wheatstone bridge or other circuit to detect or measure pressure, to process the detected or measured pressure, or for other purposes. Membrane 122 may be on the same or different side of pressure sensor 100 as bondpads 112.

Wires (not shown) may be attached to bondpads 112 using wire bonding, soldering, welding, or other technique. These wires may be bond wires, or other types of wires. After the wires are attached, an epoxy or other adhesive or potting material may be placed over bondpads 112 to insulate the bondpads and wires from each other and to secure the wires in place. Device identifier 114 may be etched in the top surface of pressure sensor 100. Device identifier 114 may be etched using a KOH etch, laser etch, DRIE, or other type of etch. Device identifier 114 may include date information, manufacturer identification information, manufacturing site identification information, mask layer revision information, and other types of information.

Unfortunately, the epoxy or other potting material applied to bondpads 112 may flow and cover all or a portion of device identifier 114, thereby making device identifier 114 impossible or difficult to read. The epoxy or other potting material may also flow and cover part or all of the pressure sensor membrane, altering the performance of the device. This may reduce yield and increase manufacturing costs.

Accordingly, these and other embodiments of the present invention may include blocking structure 116 located between device identifier 114 and bondpads 112. Blocking structure 116 may block the flow of epoxy or other potting material from bondpads 112 before it reaches device identifier 114 or membrane 122 (or both). This may prevent device identifier 114 from being obscured by the epoxy or other potting material, thereby increasing yield and reducing costs. It may also protect membrane 122 from being covered or partially covered by the epoxy or other potting material.

In these and other embodiments of the present invention, blocking structure 116 may be formed in various ways. For example, blocking structure 116 may be a trench that is formed by etching. Blocking structure 116 may be etched using a KOH etch, laser etch, DRIE, or other type of etch. Blocking structure 116 may be etched at the same time as device identifier 114. In other embodiments of the present invention, blocking structure 116 may be etched at a different time using a different step than device identifier 114.

In these and other embodiments of the present invention, blocking structure 116 may be a raised ridge or bar. This raised bar may be metallic and may be formed by deposition, plating, by forming solder bumps or other technique. Blocking structure 116 may be formed by deposition, plating, by forming solder bumps or other technique at the same time as bondpads 112. In other embodiments of the present invention, blocking structure 116 may be a raised bar formed by deposition, plating, by forming solder bumps or other technique at a different time than bondpads 112.

In these and other embodiments of the present invention, device identifier 114 may be formed by deposition, plating, by forming solder bumps or other technique. In this case, one or more, or all, of the bondpads 112, device identifier 114, and blocking structure 116 may be formed at the same time by deposition, plating, by forming solder bumps or other technique.

In other embodiments of the present invention, blocking structure 116 may include both a trench and a bar, two trenches, two bars, or other combination thereof. In these embodiments of the present invention, a bar may be between a trench and the device identifier 114 or membrane 122 (or both), a trench may be between a bar and the device identifier 114 or membrane 122 (or both), two bars may be between bondpads 112 and device identifier 114 or membrane 122 (or both), two trenches may be between bondpads 112 and device identifier 114 or membrane 122 (or both), or other arrangement may be employed. An example is shown in the following figure.

Figure 2:
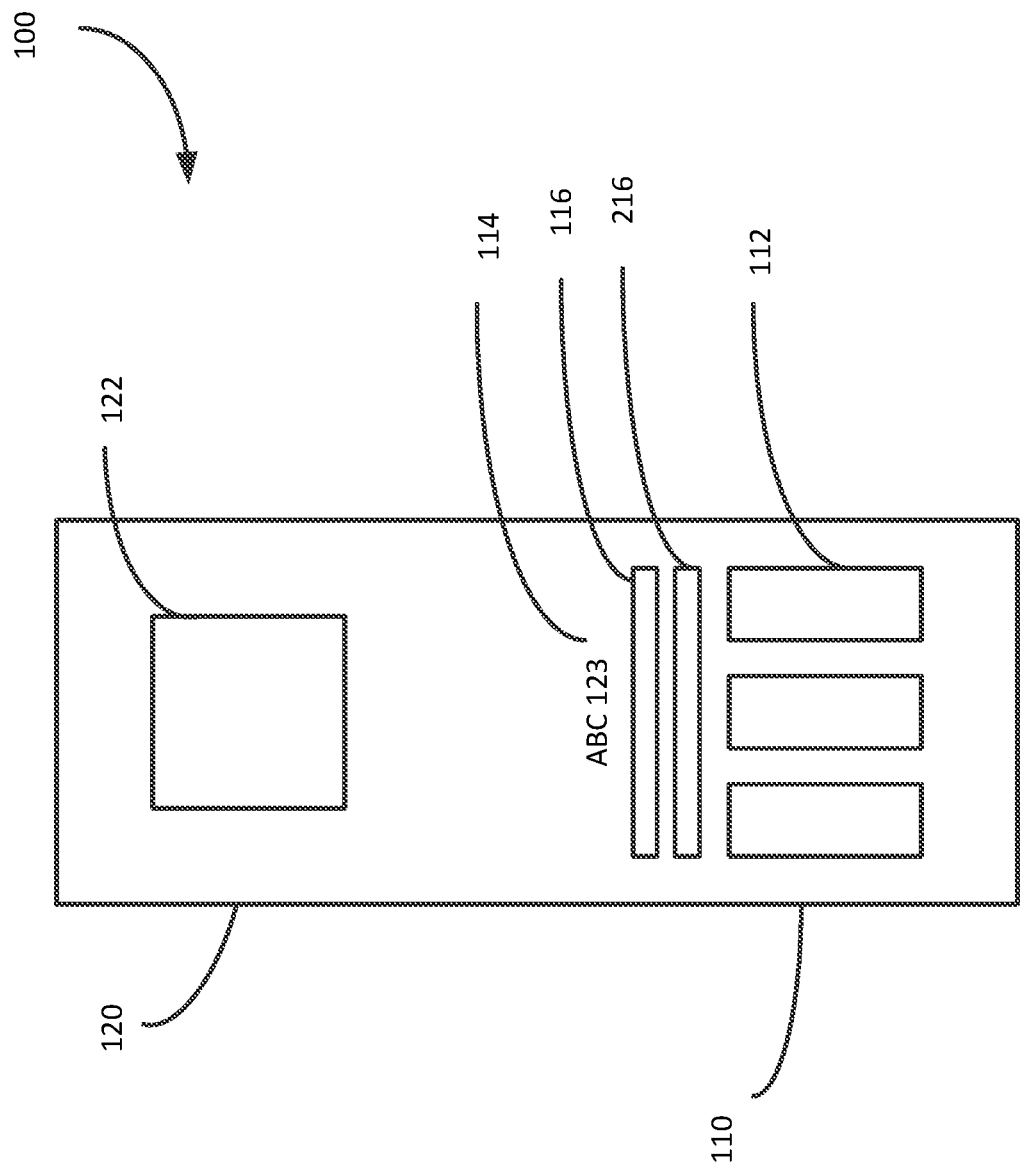
FIG. 2 is a top view of another pressure sensor having a blocking structure according to an embodiment of the present invention.

FIG. 2 is a top view of another pressure sensor according to an embodiment of the present invention. In this example, a second blocking structure 216 is shown as being between a first blocking structure 116 and bondpads 112. First blocking structure 116 may be a trench while second blocking structure 216 may be a bar, first blocking structure 116 may be a bar while second blocking structure 216 may be a trench, both blocking structures 116 and 216 may be bars, both blocking structures 116 and 216 may be trenches, or they may be other combinations of structures. Pressure sensor 200 shown here may be the same as or similar to the other pressure sensors 100, 300, 400, 500, 600, 700, 1200, or 1300 shown herein and in other embodiments of the present invention, with the addition of second blocking structure 216.

In these and other embodiments of the present invention, one or more blocking structures, such as bars and trenches, may be used and arranged in various patterns. The bar or trench used as blocking structure 116 may form a complete or partial ring around bondpads 112. Also, in these and other embodiments of the present invention, blocking structure 116 may be used to protect other features on the pressure sensor, such as other bondpads, membrane, other electrical components formed in or placed on the pressure sensor, or other structure, or any combination of the above. In each of these examples, a second blocking structure 216 may be employed as well. For example, either or both blocking structures 116 and 216 may form complete or partial rings around bondpads 112. Also, in these and other embodiments of the present invention, either or both blocking structures 116 and 216 may be used to protect other features on the pressure sensor, such as other bondpads, membrane, other electrical components formed in or placed on the pressure sensor, or other structure, or any combination of the above. Either or both blocking structures 116 and 216 may be included in this or any of the other embodiments that are shown here or are otherwise consistent with embodiments of the present invention.

To attach the wires to bondpads 112, it may be useful to provide structures to hold pressure sensor 100 in place in a fixture. An example of such a pressure sensor is shown in the following figure.

Figure 3:
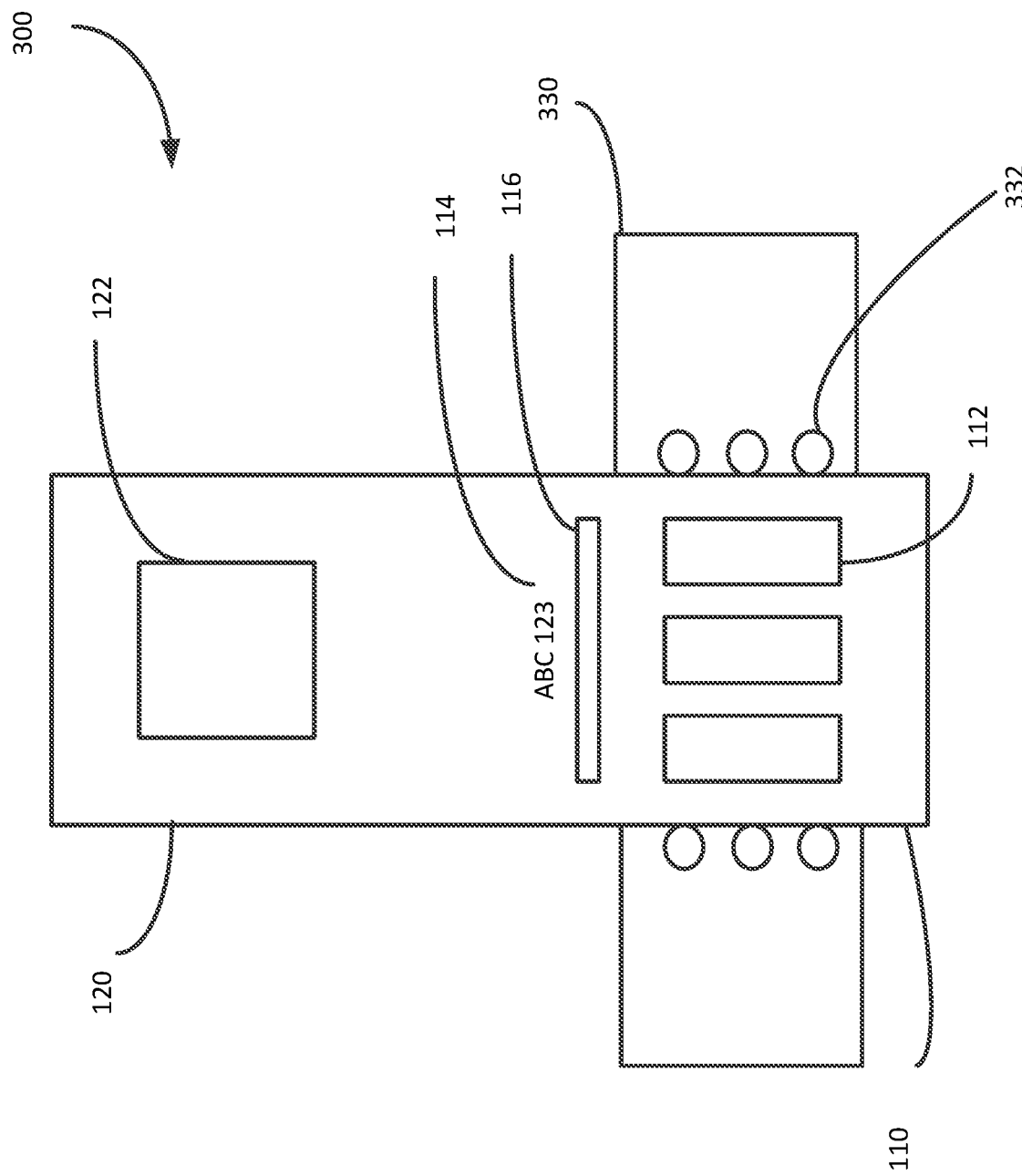
FIG. 3 is a top view of a pressure sensor having side tabs according to an embodiment of the present invention.

FIG. 3 is a top view of a pressure sensor according to an embodiment of the present invention. As before, pressure sensor 300 may include base portion 110 and handle portion 120. Base portion 110 may include bondpads 112. Handle portion 120 may include membrane 122. A number of resistors or other components (not shown) may be formed in or near membrane 122. These components may be used to form a Wheatstone bridge or other circuit to detect or measure pressure, to process the detected or measured pressure, or for other purposes.

Tabs 330 may extend laterally from sides of base portion 110. These tabs may be used to hold pressure sensor 300 in one or more fixtures during one or more manufacturing steps. These manufacturing steps may include the attachment of wires (not shown) to bondpads 112. Tabs 330 may also be used to hold pressure sensor 300 in place during the application of epoxy or other adhesive or potting material to bondpads 112 after the wires have been attached. This may simplify manufacturing, thereby increasing yield and reducing costs. As before, pressure sensor 300 may include one or more blocking structures, shown here as blocking structure 116, to protect device identifier 114, membrane 122, or both.

Tabs 330 may be removed before use of the pressure sensor 300 in various ways. For example, tabs 330 may be sawed or cut off pressure sensor 300. During this procedure, pressure sensor 300 may be held in place using tape, such as UV release tape. In these and other embodiments of the present invention, optional holes 332 may be located in tabs 330. These holes 332 may be near or adjacent to the base portion 110 in pressure sensor 300. Holes 332 may be formed by KOH etching, DRIE, laser etching, or other etching process. Holes 332 may act as perforations allowing tabs 330 to be snapped off or otherwise removed from the pressure sensor 300. In these and other embodiments of the present invention, tabs 330 may be removed by laser etching along sides of pressure sensor 300, either with or without the presence of holes 332. Tabs 330 may be included in this or any of the other embodiments that are shown here or are otherwise consistent with embodiments of the present invention. Pressure sensor 300 shown here may be the same as or similar to the other pressure sensors 100, 200, 400, 500, 600, 700, 1200, or 1300 shown herein and in other embodiments of the present invention, with the addition of tabs 330 and holes 332.

In these and other embodiments of the present invention, it may be desirable that the handle portion does not contact a housing in which the pressure sensor resides. Accordingly, in an embodiment of the present invention, the handle portion may be thinned by having a portion of its bottom side removed. An example is shown in the following figure.

Figure 4:
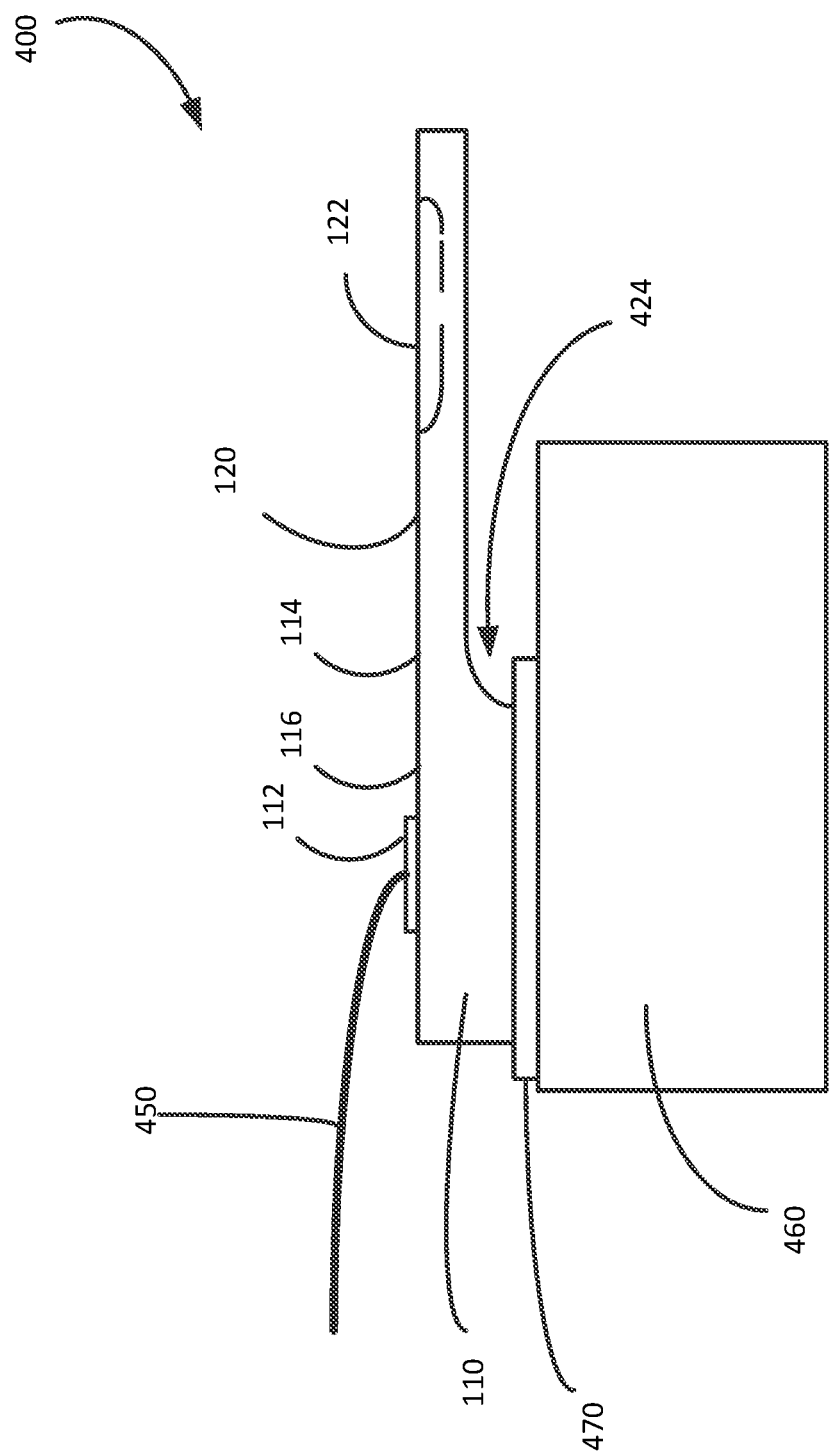
FIG. 4 is a side view of a pressure sensor having a thinned handle portion according to an embodiment of the present invention.

FIG. 4 is a side view of a pressure sensor according to an embodiment of the present invention. As in the other examples, pressure sensor 400 may include base portion 110 and handle portion 120. A number of bondpads 112 may be located on a top surface of base portion 110. Wires 450 may attach to bondpads 112 using wire bonding, soldering, welding, or other technique. A membrane 122 may be formed in a top (or bottom) surface of handle portion 120. A number of resistors or other components (not shown) may be formed on or near membrane 122. These components may be used to form a Wheatstone bridge or other circuit to detect or measure pressure, to process the detected or measured pressure, or for other purposes.

Pressure sensor 400 may be attached to housing 460 using adhesive layer 470, which may be an epoxy or other potting material or adhesive. Again, it may be undesirable for the handle portion 120 to contact the housing 460. Such contact could reduce the sensitivity of pressure sensor 400 by effectively stiffening handle portion 120. Accordingly, these and other embodiments of the present invention may provide a pressure sensor having a thinned handle portion 120. In this example, a portion of material 424 has been removed from an underside of handle portion 120, such that handle portion 120 is thinner than base portion 110. This removal of material 424 may prevent handle portion 120 from contacting housing 460 after pressure sensor 400 is installed in place. This removal may also prevent epoxy or adhesive layer 470 or other potting material from migrating under thinner handle portion 120. Such migration could again stiffen the thinner handle portion 120 leading to a reduced sensitivity of pressure sensor components formed on membrane 122. Preventing this migration may improve yields and decrease costs.

Blocking structures, such as blocking structures 116 and 216 shown in FIGS. 1 and 2, and tabs, such as tabs 330 shown in FIG. 3, may be included in this and any of the other embodiments that are shown here or are otherwise consistent with embodiments of the present invention. For example, device identifier 114 may be placed between bondpads 112 and membrane 122, while one or more blocking structures, shown here as blocking structure 116, may be placed between bondpads 112 and device identifier 114 to protect device identifier 114, membrane 122, or both. Tabs, such as tabs 330 in FIG. 3 may be included, and they may be detached in the same or similar manner. This and any of the other embodiments that are shown here or are otherwise consistent with embodiments of the present invention may be mounted on a housing and have material 424 removed in order to achieve a thinned handle portion 120. Pressure sensor 400 shown here may be substantially the same as similar to the other pressure sensors 100, 200, 300, 500, 600, 700, 1200, or 1300 shown herein or in other embodiments of the present invention.

In various embodiments of the present invention, it may be difficult to attach wires to bondpads given the small size of the pressure sensor. Accordingly, embodiments of the present invention may stagger or use alternate bondpad configurations to facilitate the bonding of wires to the bondpads. An example is shown in the following figure.

Figure 5:
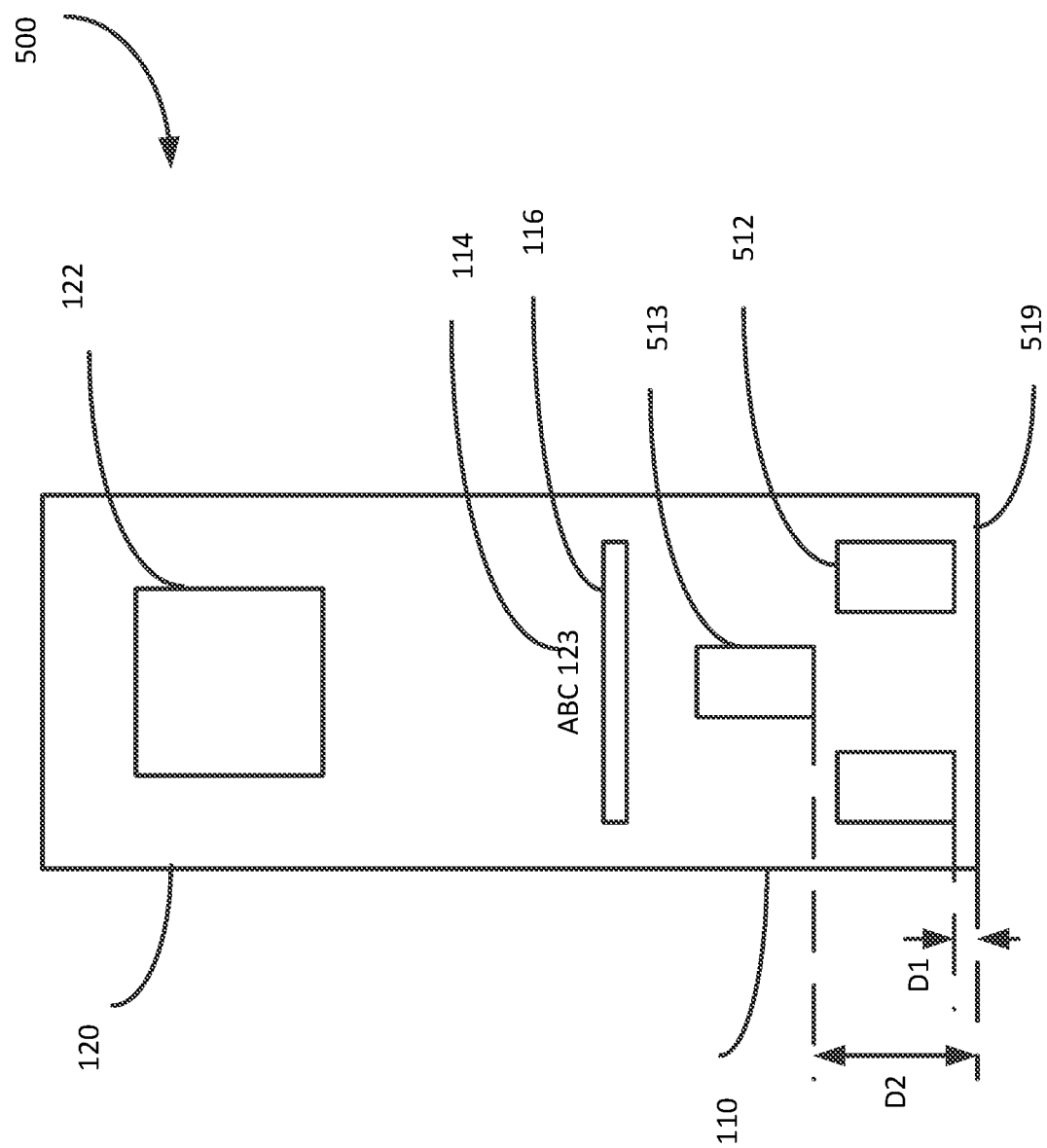
FIG. 5 is a top view of a pressure sensor having staggered bondpads according to embodiments of the present invention.

FIG. 5 is a top view of a pressure sensor according to embodiments of the present invention. As before, pressure sensor 500 may include a base portion 110 and handle portion 120. Base portion 110 may include bondpads 512 and 513, as well as device identifier 114 and blocking structure 116. Bondpads 512 and 513 may be the same as or similar to bondpads 112, and they may be bonded to and epoxied in a same or similar manner as bondpads 112. Handle portion 120 may include membrane 122. A number of resistors or other components (not shown) may be formed on or near membrane 122. These components may be used to form a Wheatstone bridge or other circuit to detect or measure pressure, to process the detected or measured pressure, or for other purposes.

In this example, the bondpads may be staggered. That is, bondpads 512 and 513 may be located at different distances D1 and D2 from a bottom edge 519 of the base portion 110 of pressure sensor 500. This may help to facilitate the attachment of wires to the bondpads, thereby improving yield and reducing costs. For example, the wires may be routed at an angle or in an orthogonal direction to the major axis of pressure sensor 500.

Blocking structures, such as blocking structures 116 and 216 shown in FIGS. 1 and 2, and tabs, such as tabs 330 shown in FIG. 3, may be included in this and any of the other embodiments that are shown here or are otherwise consistent with embodiments of the present invention. Pressure sensor 500, as with pressure sensors 100, 200, 300, 400, 600, 700, 1200, or 1300, and other pressure sensors consistent with embodiments of the present invention, may be mounted and thinned handle portion 120 may be formed as shown in FIG. 4. Pressure sensor 500 shown here may be the same as or similar to the other pressure sensors 100, 200, 300, 400, 600, 700, 1200, or 1300 show herein and in other embodiments of the present invention, with the variations in locations of bondpads 512 and 513.

In these and other embodiments of the present invention, these bondpads may be staggered in different ways. An example is shown in the following figure.

Figure 6:
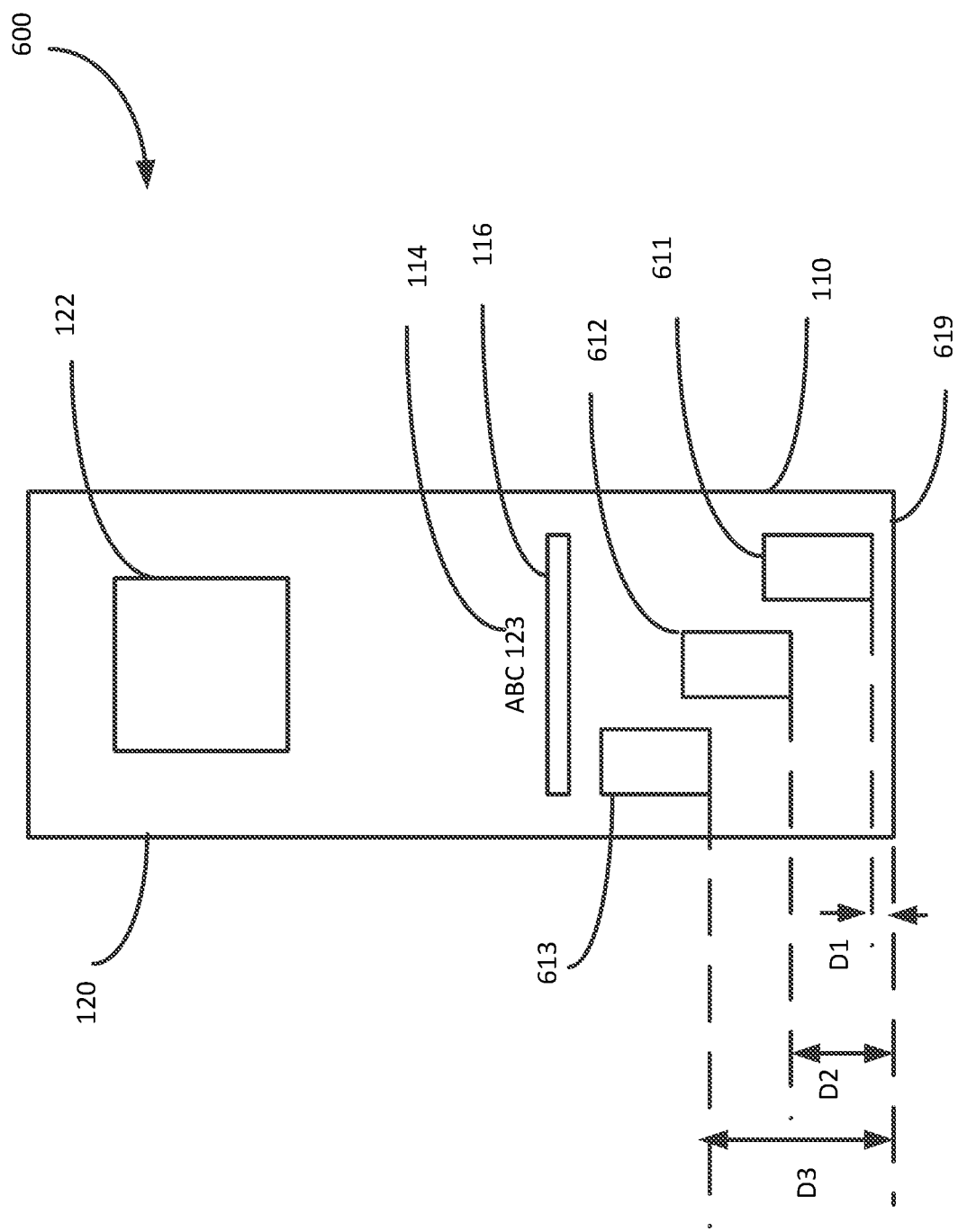
FIG. 6 is a top view of another pressure sensor having staggered bondpads according to embodiments of the present invention.

FIG. 6 is a top view of a pressure sensor according to an embodiment of the present invention. As before, pressure sensor 600 may include base portion 110 and handle portion 120. Base portion 110 may include bondpads 611, 612, and 613, as well as device identifier 114 and blocking structure 116. Bondpads 611, 612, and 613 may be the same as or similar to bondpads 112, and they may be bonded to and epoxied in a same or similar manner as bondpads 112. Handle portion 120 may include membrane 122. A number of resistors or other components (not shown) may be formed on or near membrane 122. These components may be used to form a Wheatstone bridge or other circuit to detect or measure pressure, to process the detected or measured pressure, or for other purposes.

In this example, the bondpads may be staggered. That is, bondpads 611, 612, and 613 may be located at different distances D1, D2, and D3 from a bottom edge 619 of the base portion 110 of pressure sensor 600. This may help to facilitate the attachment of wires to the bondpads, thereby improving yield and reducing costs.

Blocking structures, such as blocking structures 116 and 216 shown in FIGS. 1 and 2, and tabs, such as tabs 330 shown in FIG. 3, may be included in this and any of the other embodiments that are shown here or are otherwise consistent with embodiments of the present invention. Pressure sensor 600, as with pressure sensors 100, 200, 300, 400, 500, 700, 1200, 1300, and other pressure sensors consistent with embodiments of the present invention, may be mounted and thinned handle portion 120 may be formed as shown in FIG. 4. Pressure sensor 600 shown here may be the same as or similar to the other pressure sensors 100, 200, 300, 400, 500, 700, 1200, or 1300 shown herein and in other embodiments of the present invention, with the variations in locations of bondpads 611, 612 and 613.

In these examples, three bondpads are shown on a pressure sensor. In these and other embodiments of the present invention, a pressure sensor may have one, two, four, or more than four bondpads. These bondpads may be arranged in one of the configurations shown here, or in other configurations consistent with embodiments of the present invention.

Wires may be attached to these bondpads in order to form connections between a pressure sensor and associated devices. Accordingly, embodiments of the present invention may provide pressure sensors and associated structures that may facilitate the use of automated connection processes and tools. These and other embodiments of the present invention may provide structures for aligning interconnect wires to pressure sensor bondpads in order to facilitate the use of automated processes and tools.

Again, these pressure sensors may be too small to use in traditional semiconductor assembly tools for wire bonding or flip-chip assembly Thus, in various embodiments of the present invention, individual wires may be soldered or welded to the bondpads of the pressure sensor. To facilitate the use of automated processes and tools, embodiments of the present invention may provide structures that align wires to bondpads of a pressure sensor.

In these and other illustrative embodiments of the present invention, multiple wires may be joined together in a coplanar arrangement, where the spacings of the wires may match a spacing of the bondpads. This may be achieved using various alignment structures in these and other embodiments of the present invention. For example, the alignment structures may include a wire comb, spacers, wire insulation layers or jacket layers, or other alignment structures or combination thereof. Examples of these alignment structures are shown in the following figures.

Figure 7:
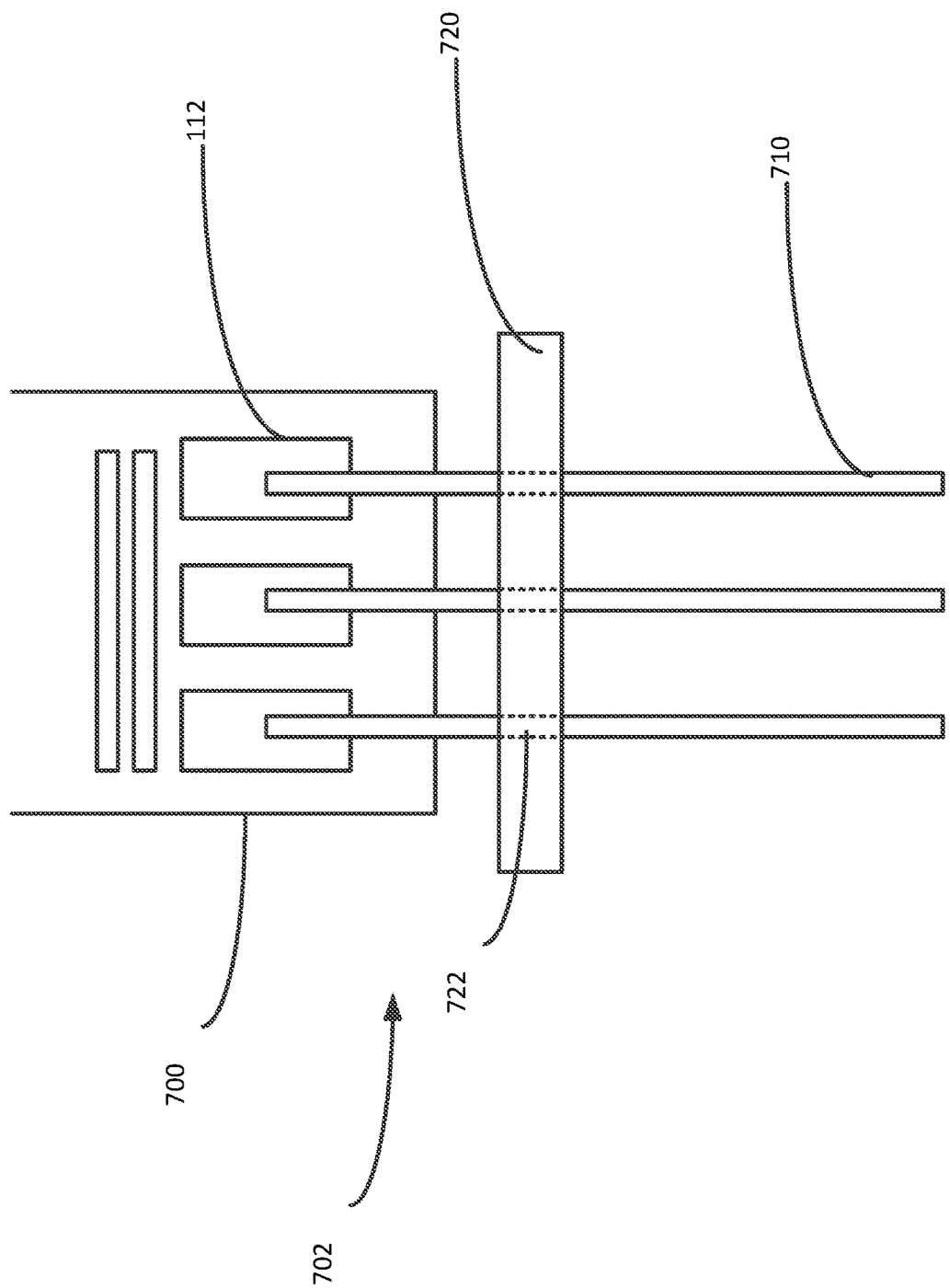
FIG. 7 illustrates a pressure sensor system including a wire comb for aligning wires to bondpads of a pressure sensor according to an embodiment of the present invention.

FIG. 7 illustrates a pressure sensor system including a wire comb for aligning wires to bondpads of a pressure sensor according to an embodiment of the present invention. Pressure sensor system 702 may include pressure sensor 700, wires 710, and wire comb 720. Pressure sensor 700, as with pressure sensors 100, 200, 300, 400, 500, 600, 1200, 1300, and other pressure sensors consistent with embodiments of the present invention, may be mounted and thinned handle portion 120 may be formed as shown in FIG. 4. Pressure sensor 700 shown here may be the same as or similar to the other pressure sensors 100, 200, 300, 400, 500, 600, 1200, or 1300 shown herein and in other embodiments of the present invention.

Wires 710 may be bare wires or they may be insulated along a portion of their length. Wires 710 may be inserted into slots along a top, bottom, or side (or combination thereof) of wire comb 720. In these and other embodiments of the present invention, wires 710 may be inserted through passages in wire comb 720.

Slots or passages 722 may be spaced to match a spacing of bondpads 112 of pressure sensor 700. More specifically, wires 710 may have the same pitch as bondpads 112. That is, wires 710 may be simultaneously aligned with centers of bondpads 112. In these and the other included examples, wires 710 may have a same or similar length, though the lengths may vary to account for staggered bondpads as shown in FIGS. 5 and 6 above. The slots or passages 722 may further match a topology of a surface of pressure sensor 700 where bondpads 112 are located. Typically this topology may be planar and wires 710 may be in a coplanar arrangement, but other topologies are possible. Wire comb 720 may hold wires 710 in place with this spacing to facilitate the use of automated processes and tools in attaching wires 710 to bondpads 112. Due to size constraints, wire comb 720 may be separate from and not attached directly to pressure sensor 700, though wire comb 720 may be attached indirectly through wires 710 to pressure sensor 700. In these and other embodiments of the present invention, wire comb 720 may be attached directly to pressure sensor 700, for example by epoxy or other potting material placed over bondpads 112. Wire comb 720 may be formed of plastic, metal, or other nonconductive or conductive material.

Figure 8:
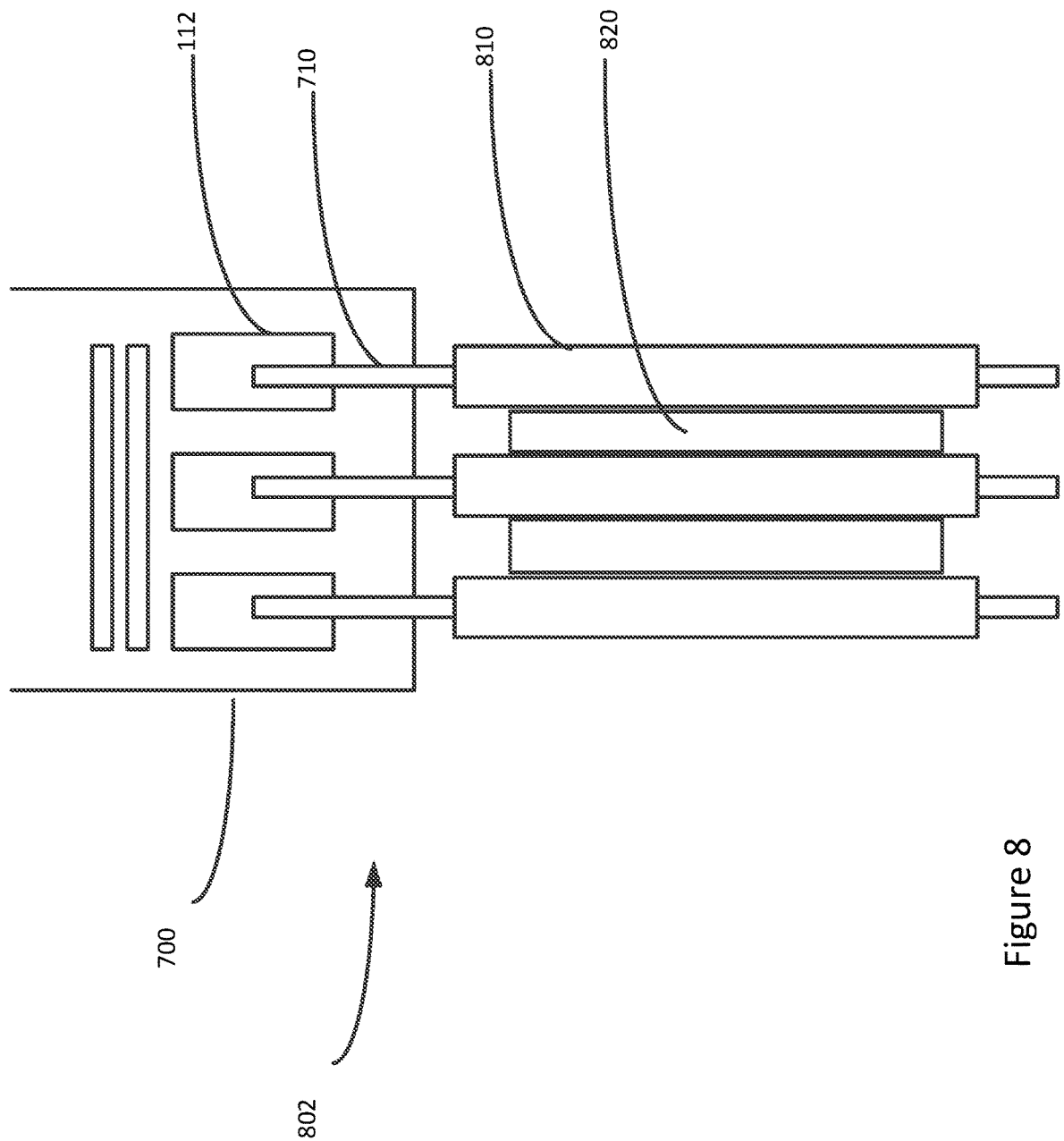
FIG. 8 illustrates a pressure sensor system including spacers for aligning wires to bondpads of a pressure sensor according to an embodiment of the present invention.

FIG. 8 illustrates a pressure sensor system including spacers for aligning wires to bondpads of a pressure sensor according to an embodiment of the present invention. Pressure sensor system 802 may include pressure sensor 700, wires 710, and spacers 820. Wires 710 may be bare wires or they may be insulated along a portion of their length. In this example, wires 710 are insulated by insulation layers 810. Spacers 820 may be between insulation layers 810 of wires 710, or they may be between and partially or fully around insulation layers 810 of wires 710.

Spacers 820 may hold wires 710 in a configuration to match a spacing of bondpads 112 of pressure sensor 700. More specifically, wires 710 may have the same pitch as bondpads 112. That is, wires 710 may be simultaneously aligned with centers of bondpads 112. In these and the other included examples, wires 710 may have a same or similar length, though the lengths may vary to account for staggered bondpads as shown in FIGS. 5 and 6 above. Spacers 820 may also hold wires 710 to match a topology of a surface of pressure sensor 700 where bondpads 112 are located. Typically this topology may be planar and wires 710 may be in a coplanar arrangement, but other topologies are possible. Spacers 820 may hold wires 710 in place with this spacing to facilitate the use of automated processes and tools in attaching wires 710 to bondpads 112. Due to size constraints, spacers 820 may be separate from and not attached directly to pressure sensor 700, though spacers 820 may be attached indirectly through wires 710 to pressure sensor 700. Spacers 820 may be formed of plastic, metal, or other nonconductive or conductive material. In these and other embodiments of the present invention, spacers 820 may be attached directly to pressure sensor 700, for example by epoxy or other potting material placed over bondpads 112. Spacers 820 may be formed of plastic, metal, or other nonconductive or conductive material.

Figure 9:
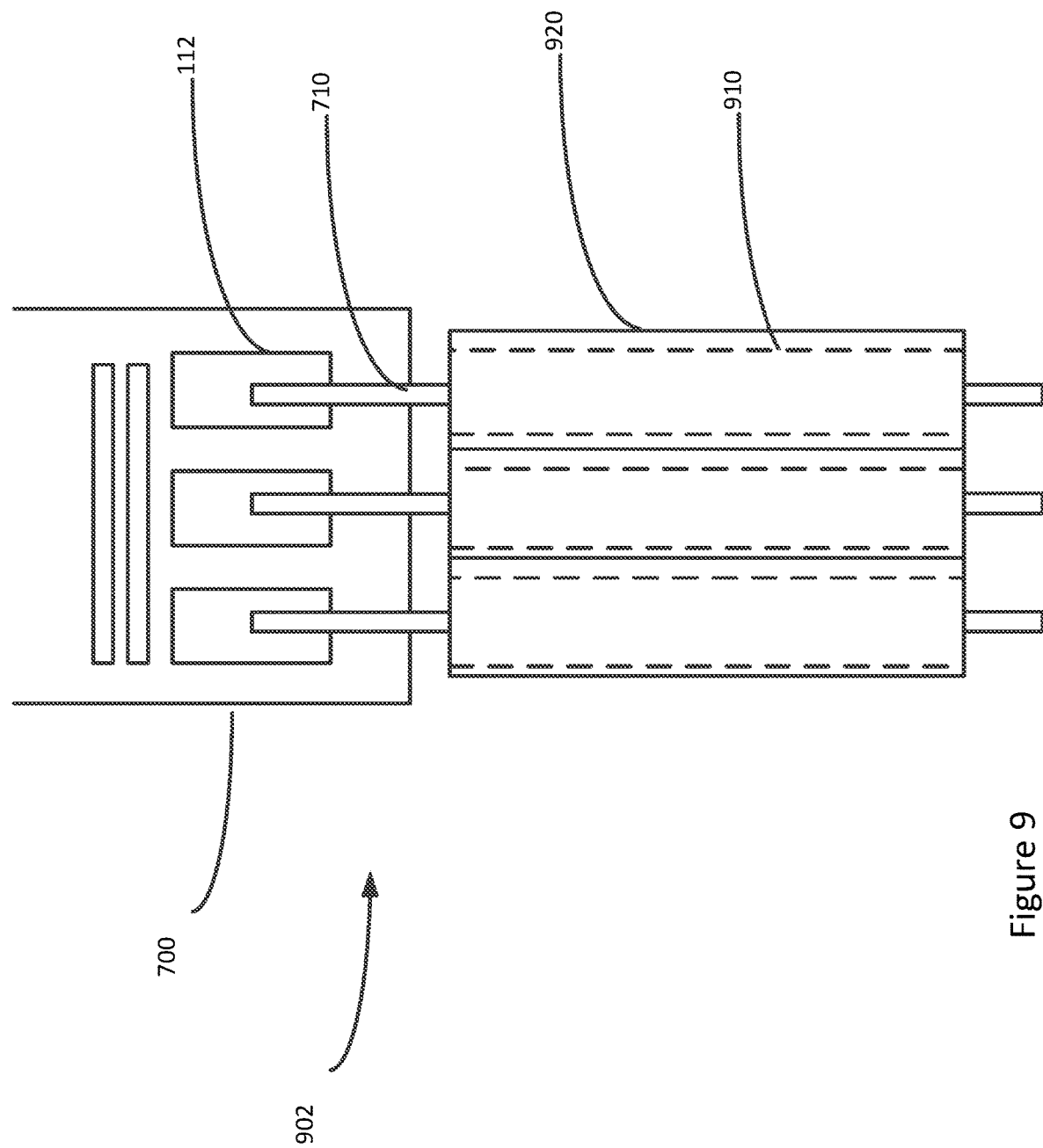
FIG. 9 illustrates a pressure sensor system including wires having a modified insulation layer for aligning wires to bondpads of a pressure sensor according to an embodiment of the present invention.

FIG. 9 illustrates a pressure sensor system including wires having a modified insulation layer for aligning wires to bondpads of the pressure sensor according to an embodiment of the present invention. Pressure sensor system 902 may include pressure sensor 700, wires 710, and insulation layers 910, which may be modified as insulation layers 920. Wires 710 may be insulated by insulation layers (or jackets) 910 along a portion of their length. Insulation layers 910 may be modified as insulation layers 920 such that wires 710 may be placed adjacent to each other to match a spacing of bondpads 112 of pressure sensor 700. That is, the insulation layer around wires 710 may be thickened, thinned, flattened or otherwise modified. In this example, insulation layer 910 may be thickened or flattened to become a wider (at least in the illustrated plane) insulation layer 920. Wires 710 may be fixed to each other with this spacing to facilitate the use of automated processes and tools in attaching wires 710 to bondpads 112. For example, wires 710 may be heated and rolled such that insulation layer 920 of wires 710 bond to insulation layer 920 of adjacent wires 710. Wires 710 may be fixed to each other either by gluing or melting together insulation layer 920 surrounding each wire 710.

Insulation layers 920 may hold wires 710 in a configuration to match a spacing of bondpads 112 of pressure sensor 700. More specifically, wires 710 may have the same pitch as bondpads 112. That is, wires 710 may be simultaneously aligned with centers of bondpads 112. In these and the other included examples, wires 710 may have a same or similar length, though the lengths may vary to account for staggered bondpads as shown in FIGS. 5 and 6 above. Wires 710 may also be arranged to match a topology of a surface of pressure sensor 700 where bondpads 112 are located. Typically this topology may be planar and wires 710 may be in a coplanar arrangement, but other topologies are possible. Due to size constraints, insulation layer 920 around wires 710 may be separate from and may not typically be attached directly to pressure sensor 700. In these and other embodiments of the present invention, insulation layer 920 may be attached directly to pressure sensor 700, for example by epoxy or other potting material placed over bondpads 112. In these and other embodiments of the present invention, the insulation layer or layers 920 may be formed of plastic, polymers, or other material, and may be formed by extrusion or other process.

Figure 10:
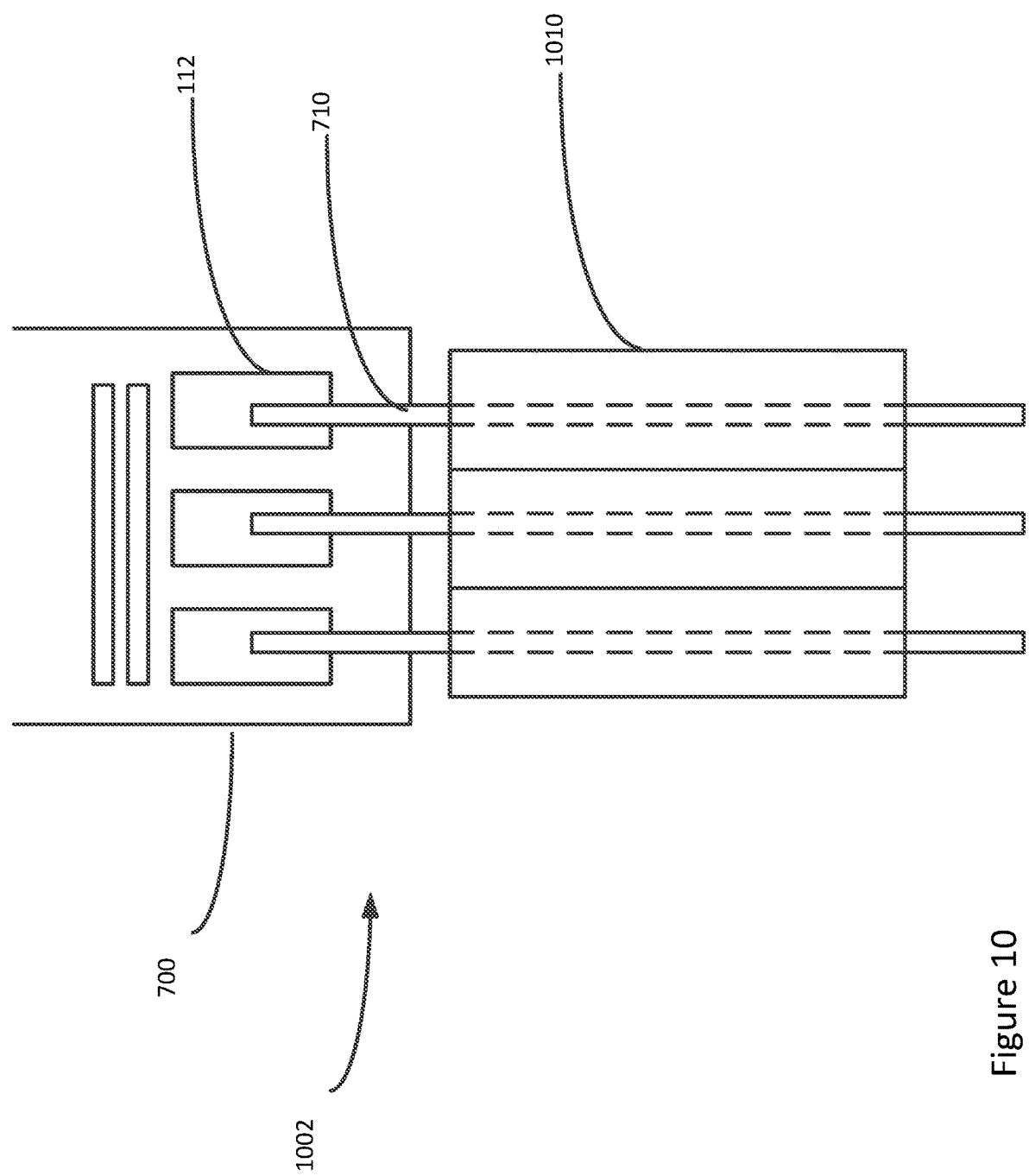
FIG. 10 illustrates a pressure sensor system including wires having an insulation layer that is formed such that adjacent wires are aligned with bondpads of a pressure sensor according to an embodiment of the present invention.

FIG. 10 illustrates a pressure sensor system including wires having an insulation layer that is formed such that adjacent wires are aligned with bondpads of the pressure sensor according to an embodiment of the present invention. Pressure sensor system 1002 may include pressure sensor 700, wires 710, and insulation layers 1010. Wires 710 may be insulated along a portion of their length. Insulation layer 1010 may be formed around each wire such that wires 710 may be placed adjacent to each other and have a resulting spacing that matches a spacing of bondpads 112 of pressure sensor 700. That is, insulation layer 1010 around wires 710 may be the thickness that is needed to provide a spacing between wires 710 that matches a spacing between bondpads 112. Wires 710 may be fixed to each other with this spacing to facilitate the use of automated processes and tools in attaching wires 710 to bondpads 112. For example, wires 710 may be heated and rolled such that the insulation layer of wires 710 bond to the insulation layer of adjacent wires.

Again, insulation layers 1010 may hold wires 710 in a configuration to match a spacing of bondpads 112 of pressure sensor 700. More specifically, wires 710 may have the same pitch as bondpads 112. That is, wires 710 may be simultaneously aligned with centers of bondpads 112. In these and the other included examples, wires 710 may have a same or similar length, though the lengths may vary to account for staggered bondpads as shown in FIGS. 5 and 6 above. Wires 710 may also be arranged to match a topology of a surface of pressure sensor 700 where bondpads 112 are located. Typically this topology may be planar and wires 710 may be in a coplanar arrangement, but other topologies are possible. Due to size constraints, insulation layer 1010 around wires 710 may be separate from and may not typically be attached directly to pressure sensor 700. In these and other embodiments of the present invention, insulation layer 1010 may be attached directly to pressure sensor 700, for example by epoxy or other potting material placed over bondpads 112. In these and other embodiments of the present invention, the insulation layer or layers 1010 may be formed of plastic, polymers, or other material, and may be formed by extrusion or other process.

Figure 11:
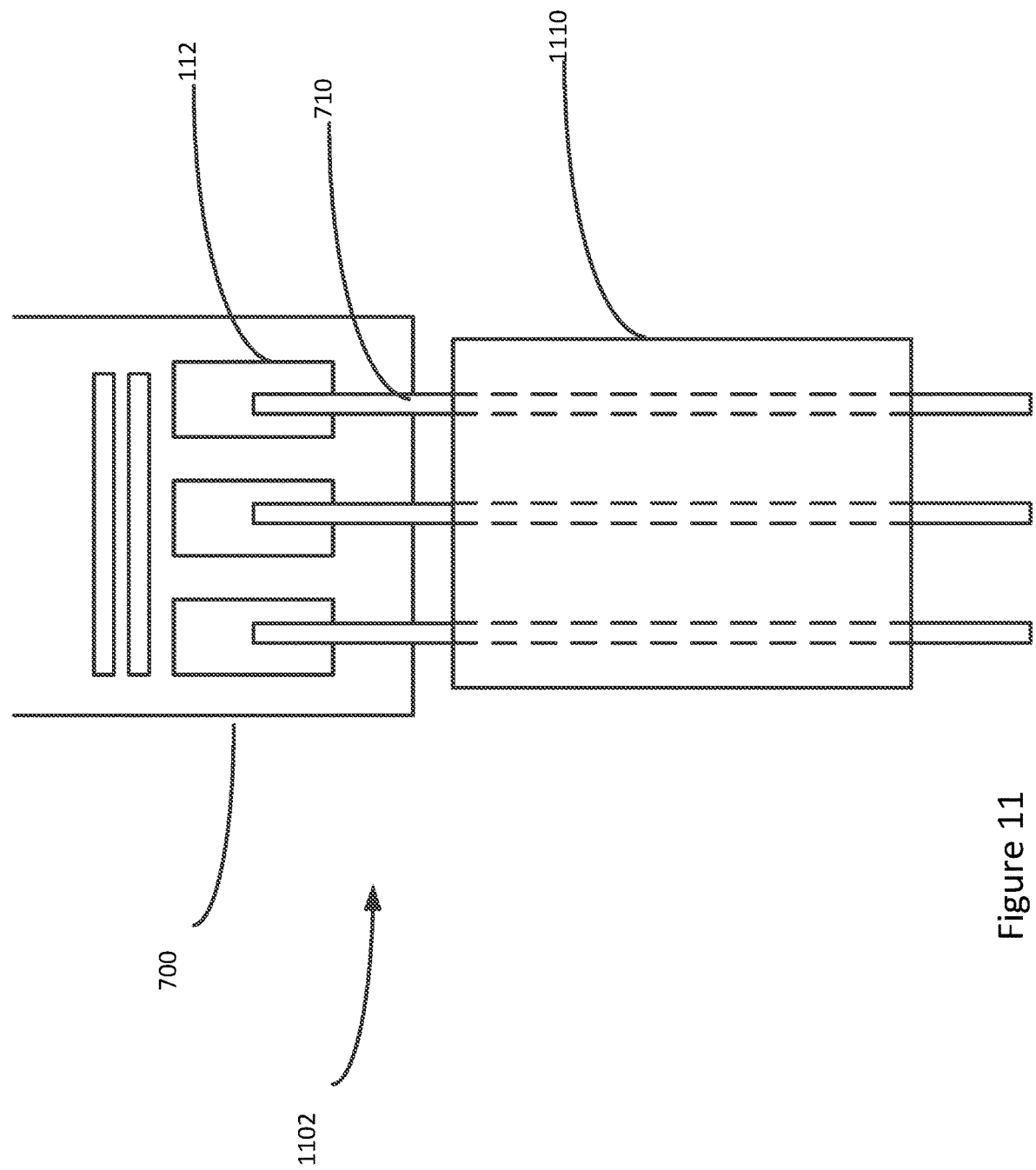
FIG. 11 illustrates a pressure sensor system including a plurality of wires having a common insulation layer that is formed for aligning the wires to bondpads of a pressure sensor according to an embodiment of the present invention.

FIG. 11 illustrates a pressure sensor system including a plurality of wires having a common insulation layer that is formed for aligning wires to bondpads of the pressure sensor according to an embodiment of the present invention. Pressure sensor system 1102 may include pressure sensor 700, wires 710, and common insulation layer 1110. Wires 710 may be insulated along a portion of their length by a common insulation layer 1110. For example, wires 710 may be placed such that they have a spacing that matches a spacing of bondpads 112. Common insulation layer 1110 may then be formed around wires 710. Common insulation layer 1110 may fix wires 710 to each other with this spacing to further facilitate the use of automated equipment.

Again, common insulation layer 1110 may hold wires 710 in a configuration to match a spacing of bondpads 112 of pressure sensor 700. More specifically, wires 710 may have the same pitch as bondpads 112. That is, wires 710 may be simultaneously aligned with centers of bondpads 112. In these and the other included examples, wires 710 may have a same or similar length, though the lengths may vary to account for staggered bondpads as shown in FIGS. 5 and 6 above. Wires 710 may also be arranged to match a topology of a surface of pressure sensor 700 where bondpads 112 are located. Typically this topology may be planar and wires 710 may be in a coplanar arrangement, but other topologies are possible. Due to size constraints, common insulation layer 1110 around wires 710 may be separate from and may not typically be attached directly to pressure sensor 700. In these and other embodiments of the present invention, insulation layer 1110 may be attached directly to pressure sensor 700, for example by epoxy or other potting material placed over bondpads 112. In these and other embodiments of the present invention, the insulation layer or layers 1110 may be formed of plastic, polymers, or other material, and may be formed by extrusion or other process.

Automated processes and tools may be employed to electrically and physically join wires 710 to pressure sensor 700 bondpads. First, the insulation layer may be stripped from wires 710, which may be done with a laser or lasers, but may also be accomplished with heat, chemical, or mechanical means, for example by chemical etching. The exposed conductors of wires 710 may then be cut, preferably without damaging or bending wires 710, or otherwise destroying the spacing required for automated assembly. Laser cutting may be used for this purpose.

The now-isolated wire tips can now be aligned with bondpads 112 of pressure sensor 700. Various methods may be employed to electrically and physically join wires 710 to bondpads 112. For example, bondpads 112 may be coated with a solder during wafer manufacture. The die may then be heated to melt the solder, and then wires 710 may be brought into contact with the molten solder. Once this has been achieved the heat source may be removed, allowing the solder to cool and harden onto the wire 710. Wires 710 may be attached one at a time, two or more at a time, or all wires may be attached in a single operation.

These and other embodiments of the present invention may use compression bonding to attach wires 710 to bondpads 112. In these and other embodiments of the present invention, two closely-spaced electrodes may be brought into contact with wire 710. A current may be passed from one electrode through wire 710 and to the second electrode. The electrodes may be pressed down on wire 710, and the combination of heat and pressure may weld wires 710 to bondpads 112. In these and other embodiments of the present invention, during compression bonding, no current is passed through wire 710. Instead, current is passed through a highly-resistive region between the two electrodes, resulting in heat generation. The electrodes are pressed down on wire 710, and the combination of heat and pressure may weld wires 710 to bondpads 112. Wires 710 may be attached one at a time, two or more at a time, or all wires may be attached in a single operation.

These and other embodiments of the present invention may instead rely on heat and pressure applied to wires 710. The sensors may be placed on a hotplate or the heat may be applied from above wires 710 as wires 710 are pressed onto bondpads 112. Wires 710 may be attached one at a time, two or more at a time, or all wires may be attached in a single operation.

To electrically isolate bondpads 112 from one another, these and other embodiments of the present invention may cover bondpads 112 of pressure sensor 700, along with wires 710 that are soldered or otherwise attached to them, with an insulating material such as epoxy, adhesive, sealant, potting material or substance or the like. In addition to providing an electrical insulation layer, this may provide mechanical protection of the delicate solder bonds during assembly, shipping and operation. This material may be dispensed in liquid form and then cured by heat, exposure to humidity, UV irradiation or similar techniques. Unfortunately, the flow of the epoxy or other sealant may be difficult to control, and the techniques described above may be employed.

These and other embodiments of the present invention may provide pressure sensors that may be used in various applications. For example, they may be used in catheters, biopsy equipment, or other medical applications and other types of applications. In some of these applications, a pressure sensor may be exposed to light, such as from an endoscope. In some embodiments of the present invention, this may be desirable (or ignorable) and it may not be necessary to take preventive measures. In other embodiments of the present invention, the presence of light may shift or alter pressure sensor readings in an undesirable manner. For example, light may change characteristics of p-n junctions of resistors, transistors, or other components on or near the pressure sensor membrane. This may alter measured resistance values or other parameters of the components, thereby skewing the resulting pressure readings in an undesirable manner.

Accordingly, embodiments of the present invention may provide structures for blocking light for all or some of the components on a pressure sensor. For example, a pressure sensor may be placed in an opaque package or housing. In these and other embodiments of the present invention, a layer of metal or other material may be formed over some or all of a number of components on or near a membrane of the pressure sensor. This layer may be gold, copper, aluminum or other material. This layer may be attached to pressure sensor 700 using a material with an adhesive quality, such as tantalum, titanium-tungsten, titanium, chromium, or other metal or other material. That is, the layer may be over an adhesion layer of tantalum, titanium-tungsten, titanium, chromium, or other metal or other material. The material for the layer, as well as the adhesion layer, may be chosen for its softness or other property such that its presence has a minimized effect on characteristics of the pressure sensor. These layers may be formed by physical vapor deposition (PVD), plating, sputtering, or other process. In these and other embodiments of the present invention, one or more layers of a pressure sensor may be altered or modified, or additional layers may be added, such that they reduce or block light. For example, antireflective coatings, such as buried antireflective coatings, may be used to block light from reaching the p-n junctions of the pressure sensor components.

In these and other embodiments of the present invention, the layer of metal over the membrane may form a light shield to block light from reaching components on the membrane. This light shield may be protected by encapsulation with epoxy or other material. But since the pressure sensor may be inserted in a human body, it may be desirable to reduce its size. Accordingly, embodiments of the present invention may leave the light shield exposed and not encapsulated with epoxy or other substances. In these and other embodiments of the present invention, a thin protective layer, as opposed to a full encapsulation, may be applied over the light shield.

Since the light shield may be exposed and not encapsulated, it may come into direct contact with human body tissue during its use. Accordingly, the light shield may be left electrically floating and not connected to ground or other voltage potential. This may help to prevent the formation of electrical pathways through the human body and pressure sensor. It may also prevent reduced battery life from electrical leakage pathways in battery-powered devices.

It may also be desirable to be able to track a temperature of the pressure sensor's environment. Unfortunately, there may not be sufficient area to place temperature sensing circuitry on the pressure sensor. Instead, measurements of resistors on the membrane may be made. Temperature changes may cause each resistor on the membrane to change in the same way. This is in contrast to changes in pressure, which may cause each resistors to change differently. Accordingly, these two effects may be separated to track temperature and pressure independently. Calibration and testing routines may be done during or after manufacturing to generate data tables and formulae that may be used to translate resistance changes to pressure and temperature variations. An example of a pressure sensor with such a light shield is shown in the following figure.

Figure 12:
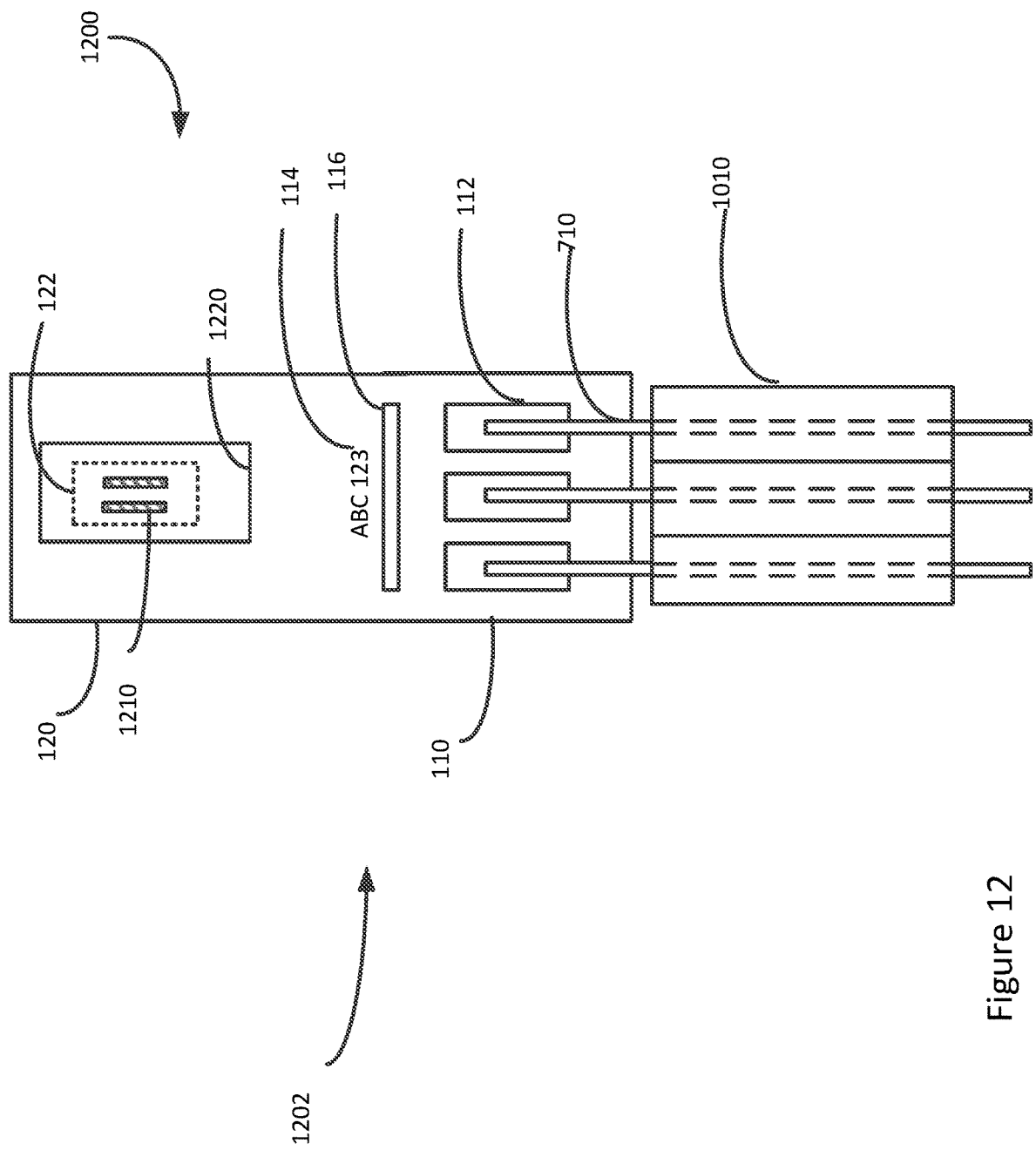
FIG. 12 illustrates a pressure sensor system including a light-reducing or blocking structure according to an embodiment of the present invention.

FIG. 12 illustrates a pressure sensor system including a light-reducing or blocking structure on a pressure sensor according to an embodiment of the present invention. In this example, pressure sensor system 1202 may include pressure sensor 1200, wires 710, and insulating layers 1010. Pressure sensor 1200, as with pressure sensors 100, 200, 300, 400, 500, 600, 700, 1300, and other pressure sensors consistent with embodiments of the present invention, may be mounted and thinned handle portion 120 may be formed as shown in FIG. 4. Pressure sensor 1200 shown here may be the same as or similar to the other pressure sensors 100, 200, 300, 400, 500, 600, 700, or 1300 shown herein and in other pressure sensors consistent with embodiments of the present invention.

Pressure sensor 1200 may include base portion 110 and handle portion 120. Base portion 110 may include a number of bondpads 112. Handle portion 120 may include membrane 122. One or more components 1210 may be located on or near (for example, on an edge of) membrane 122. Components 1210 may be resistors, transistors, or other passive or active components. In this example, light shield 1220 formed of a layer of metal or other material may be formed over some or all of a number of components 1210 on or near membrane 122 of pressure sensor 1200. Light shield 1220 may be gold, copper, aluminum or other material. This light shield 1220 may be attached to pressure sensor 1200 using a material with an adhesive quality, such as tantalum, titanium-tungsten, titanium, chromium, or other metal or other material. That is, light shield 1220 may be over an adhesion layer of tantalum, titanium-tungsten, titanium, chromium, or other metal or other material. The material for the light shield, as well as the adhesion layer, may be chosen for its softness or other property such that its presence has a minimized effect on characteristics of components 1210 of pressure sensor 1200. Light shield 1220, and its adhesive layer if present, may be formed by physical vapor deposition (PVD), plating, sputtering, or other process. In these and other embodiments of the present invention, one or more other layers (not shown) of pressure sensor 1200 may be altered or modified, or additional layers may be added, such that they reduce or block light. For example, antireflective coatings, such as buried antireflective coatings, may be used to block light from reaching the p-n junctions of the pressure sensor components 1210.

In these and other embodiments of the present invention, light shield 1220 may be protected by encapsulation with epoxy or other material (not shown.) But since pressure sensor system 1202 may be inserted in a human body, it may be desirable to reduce its size. Accordingly, embodiments of the present invention may leave light shield 1220 exposed and not encapsulated with epoxy or other substances. In these and other embodiments of the present invention, a thin protective layer (not shown), as opposed to a full encapsulation, may be applied over light shield 1220.

Since light shield 1220 may be exposed and not encapsulated, it may come into direct contact with human body tissue during its use. Accordingly, light shield 1220 may be left electrically disconnected or floating and not connected to ground or other voltage potential. This may help to prevent the formation of electrical pathways through the human body and pressure sensor 1200. It may also prevent reduced battery life from electrical leakage pathways in battery-powered devices.

It may also be desirable to be able to track a temperature of the pressure sensor's environment. Unfortunately, there may not be sufficient area to place temperature sensing circuitry on the pressure sensor 1200. Instead, measurements of resistors on the membrane may be made. Temperature changes may cause each resistor or other component 1210 on membrane 122 to change in the same way. This is in contrast to changes in pressure, which may cause each resistor or other components 1210 to change differently. Accordingly, these two effects may be separated to track temperature and pressure independently. Calibration and testing routines may be done during or after manufacturing to generate data tables and formulae that may be used to translate resistance changes to pressure and temperature variations.

As shown in FIG. 1, pressure sensor 1200 may include device identifier 114 and blocking structure 116. As shown in FIG. 10, wires 710 may be insulated by insulating layers 1010. Insulating layers 1010 may have a thickness such that when the insulating layers are adjacent, wires 710 align with bondpads 112 on pressure sensor 1200.

The wires and bondpads in these pressure sensor systems may be arranged symmetrically in a lateral direction. This may result in the wires being attached to the bondpads in a reversed or mirrored configuration during assembly. This error in attachment may necessitate reworking of the pressure sensor system and may even result in yield loss. Accordingly, embodiments of the present invention may provide alignment structures that are asymmetrical. For example, where wires are held in a wire comb, the slots or openings in the wire comb may be unevenly spaced in a lateral direction. The bondpads on the pressure sensor may also be unevenly spaced in the lateral direction. In other embodiments of the present invention, spacers may provide different spacings. In still other embodiments of the present invention, wires may have mismatched widths for their insulation layers. In these embodiments, it should be noted that the wires may not be coplanar due to the mismatched insulation layer widths. An example employing spacers of different widths is shown in the following figure.

Figure 13:
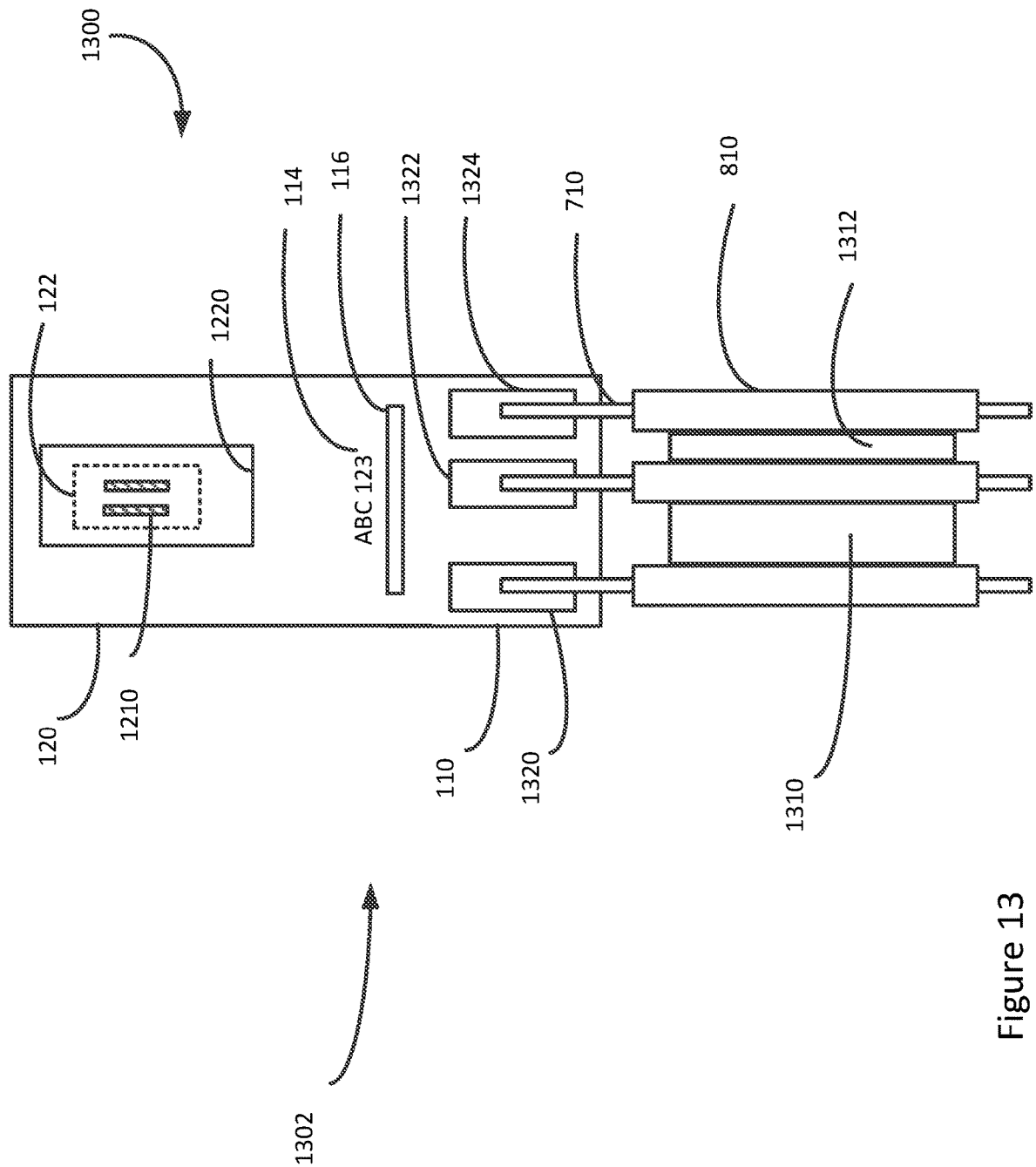
FIG. 13 illustrates a pressure sensor system having laterally staggered bondpads according to an embodiment of the present invention.

FIG. 13 illustrates a pressure sensor system having laterally staggered bondpads according to an embodiment of the present invention. In this example, pressure sensor system 1302 may include pressure sensor 1300 and wires 710 having insulating layers 810. Pressure sensor 1300, as with pressure sensors 100, 200, 300, 400, 500, 600, 700, 1200, and other pressure sensors consistent with embodiments of the present invention, may be mounted and thinned handle portion 120 may be formed as shown in FIG. 4. Pressure sensor 1300 shown here may be the same as or similar to the other pressure sensors 100, 200, 300, 400, 500, 600, 700, or 1200 shown herein and in other pressure sensors consistent with embodiments of the present invention.

Pressure sensor 1300 may include base portion 110 and handle portion 120. Base portion 110 may include a number of bondpads 1320, 1322, and 1324. Bondpads 1320, 1322, and 1324 may be unevenly spaced. For example, bondpad 1320, which may be a ground pad in various embodiments of the present invention, may be spaced to one side. This may give a unique position to each of the other bondpads 1322 and 1324, which may be resistor pads in various embodiments of the present invention. To compensate for the uneven bondpad spacing, spacer 1310 may be wider than spacer 1312. That is, a first spacer 1310 that is between a first wire and a second wire may be thicker than a second spacer 1312 that is between the second wire and a third wire. The wider spacer 1310 may align wires 710 to bondpads 1320, 1322, and 1324 when wires 710 are properly oriented. When wires 710 are flipped or reversed, the wider spacer 1310 may misalign wires 710 to bondpads 1320, 1322, and 1324 making the reversal of wires 710 more obvious. This may avoid confusion when wires 710 are attached to pressure sensor 1300 and makes a reversed or mirrored attachment less likely.

As shown in FIG. 1, pressure sensor 1300 may include device identifier 114 and blocking structure 116. As shown in FIG. 12, handle portion 120 may include membrane 122. One or more components 1210 may be located on or near (for example, on an edge of) membrane 122. Components 1210 may be resistors, transistors, or other passive or active components. In this example, a light shield 1220 of metal or other material may be formed over some or all of a number of components 1210 on or near membrane 122 of pressure sensor 1300 in order to block light. Light shield 1220 may be formed of gold, copper, aluminum or other material. This light shield 1220 may be attached to the pressure sensor 1300 using a material with an adhesive quality, such as tantalum, titanium-tungsten, titanium, chromium, or other metal or other material. That is, light shield 1220 may be over a layer of tantalum, titanium-tungsten, titanium, chromium, or other metal or other material.

The above description of embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated. Thus, it will be appreciated that the invention is intended to cover all modifications and equivalents within the scope of the following claims.

What is claimed is:

1. A pressure sensor system comprising:
   a pressure sensor comprising:
   a membrane;
   a plurality of components on the membrane;
   a plurality of bondpads on the pressure sensor, the plurality of bondpads having a first spacing; and
   a light shield formed by depositing a first layer over the plurality of components on the membrane.

2. The pressure sensor system of claim 1 wherein the light shield is electrically floating.

3. The pressure sensor system of claim 2 further comprising:
   a plurality of wires, each wire attached to a corresponding one of the plurality of bondpads; and
   an alignment structure to space the plurality of wires such that adjacent wires in the plurality of wires have the first spacing.

4. The pressure sensor system of claim 3 wherein the alignment structure is separate from the pressure sensor.

5. The pressure sensor system of claim 4 wherein the alignment structure comprises insulation layers around each of the plurality of wires.

6. The pressure sensor system of claim 4 wherein the alignment structure comprises an insulation layer around each of the plurality of wires.

7. The pressure sensor system of claim 3 further comprising a blocking structure between the bondpads and the membrane.

8. The pressure sensor system of claim 7 wherein the blocking structure comprises a trench.

9. The pressure sensor system of claim 1 wherein the light shield is electrically disconnected from the pressure sensor system.

10. A pressure sensor system comprising:
    a pressure sensor comprising:
    a membrane;
    a plurality of components located on or near the membrane;
    a light shield over the plurality of components; and
    a plurality of coplanar bondpads; and
    a plurality of wires, each having an exposed portion on at least one end of the wire; and
    an alignment structure to space the plurality of wires such that spacings of the exposed portions of adjacent wires in the plurality of wires match spacings of adjacent bondpads in the plurality of bondpads, the alignment structure separate from the pressure sensor.

11. The pressure sensor system of claim 10 wherein the light shield is electrically floating.

12. The pressure sensor system of claim 11 wherein the alignment structure comprises insulation layers surrounding each wire.

13. The pressure sensor system of claim 11 wherein the alignment structure comprises an insulation layer surrounding the plurality of wires.

14. The pressure sensor system of claim 10 wherein the light shield is electrically disconnected from the pressure sensor system.

15. The pressure sensor system of claim 10 wherein the light shield is formed by depositing a metal layer.

16. The pressure sensor of claim 15 wherein the light shield is electrically floating.

17. A pressure sensor system comprising:
    a pressure sensor comprising:
    a plurality of bondpads;
    a membrane;
    a component on or near the membrane; and
    a light-reducing layer deposited over the component; and
    a plurality of wires, each having an exposed portion on at least one end of the wire, each wire connected to a corresponding one of the plurality of bondpads.

18. The pressure sensor system of claim 17 wherein the light-reducing layer is a metallic layer that is electrically floating.

19. The pressure sensor system of claim 17 wherein the light-reducing layer is a metallic layer that is electrically disconnected form the pressure sensor system.

20. The pressure sensor system of claim 17 wherein the light-reducing layer is a light shield formed of a metallic layer.

21. The pressure sensor system of claim 20 wherein the metallic layer is formed of a gold layer, and wherein the gold layer is over a layer comprising one of tantalum, titanium-tungsten, or titanium.

22. The pressure sensor system of claim 20 wherein the component is a resistor.

* * * * *